(12) United States Patent
Skajster

(10) Patent No.: US 10,918,395 B2
(45) Date of Patent: Feb. 16, 2021

(54) SURGICAL MILLING CUTTER

(71) Applicant: Skajster Familienstiftung, Triesen (LI)

(72) Inventor: Tomasz Jan Skajster, Bochum (DE)

(73) Assignee: SKAJSTER FAMILIENSTIFTUNG, Triesen (LI)

( * ) Notice: Subject to any disclaimer, the term of this patent is extended or adjusted under 35 U.S.C. 154(b) by 0 days.

(21) Appl. No.: 16/095,206

(22) PCT Filed: Apr. 24, 2017

(86) PCT No.: PCT/EP2017/059670
§ 371 (c)(1),
(2) Date: Oct. 19, 2018

(87) PCT Pub. No.: WO2017/182673
PCT Pub. Date: Oct. 26, 2017

(65) Prior Publication Data
US 2019/0142438 A1    May 16, 2019

(30) Foreign Application Priority Data

Apr. 22, 2016  (DE) .................. 10 2016 107 549
Aug. 11, 2016  (DE) .................. 20 2016 104 435 U

(51) Int. Cl.
*A61B 17/16*   (2006.01)
*A61B 90/00*   (2016.01)

(52) U.S. Cl.
CPC ...... *A61B 17/1617* (2013.01); *A61B 17/1615* (2013.01); *A61B 17/1671* (2013.01);
(Continued)

(58) Field of Classification Search
CPC ........ A61B 2017/1602; A61B 17/1615; A61B 17/1671
See application file for complete search history.

(56) References Cited

U.S. PATENT DOCUMENTS 2,723,455 A   11/1955 Oberley
2,753,618 A    7/1956 Stanziale
(Continued)

FOREIGN PATENT DOCUMENTS

DE   19634484 C1   4/1998
DE   10022047 C1   9/2001
(Continued)

OTHER PUBLICATIONS

Office Action dated Feb. 5, 2019 in EP Application No. 17720429.4.
(Continued)

*Primary Examiner* — Si Ming Ku
(74) *Attorney, Agent, or Firm* — Panitch Schwarze Belisario & Nadel LLP

(57) ABSTRACT

A surgical milling cutter designed to remove bone and/or cartilage tissue includes a shaft which extends along a longitudinal axis, can rotate about same, and can be releasably connected to a drive device and which has a proximal end that can be rotationally fixed to a drive unit and a distal end lying opposite the proximal end. A milling surface circumferentially surrounds the shaft (2) and extends on the distal end along the longitudinal axis of the shaft. The milling surface protrudes radially from the shaft and has a milling surface maximum radius. The surgical milling cutter prevents unwanted damage to delicate body structures via an atraumatic design having a protective assembly provided on the distal end. The protective assembly has a distal support surface and a protective assembly maximum radius in order to form a protective ring which surrounds the milling surface maximum radius in a circular manner.

27 Claims, 24 Drawing Sheets

(52) U.S. Cl.
CPC ...... *A61B 17/1679* (2013.01); *A61B 17/1688* (2013.01); *A61B 2017/1602* (2013.01); *A61B 2090/036* (2016.02)

(56) References Cited

U.S. PATENT DOCUMENTS

| | | | |
|---|---|---|---|
| 2,807,264 | A | 9/1957 | Tuck |
| 6,162,227 | A | 12/2000 | Eckhardt et al. |
| 6,186,788 | B1 | 2/2001 | Massad |
| 7,189,240 | B1 * | 3/2007 | Dekel ................ A61B 17/1671 606/84 |
| 2004/0133209 | A1 * | 7/2004 | Chappuis ........... A61B 17/1617 606/80 |
| 2006/0106393 | A1 * | 5/2006 | Huebner .............. A61B 17/164 606/80 |
| 2008/0306483 | A1 | 12/2008 | Iannarone |
| 2015/0354635 | A1 | 12/2015 | Mcclymont et al. |

FOREIGN PATENT DOCUMENTS

| | | |
|---|---|---|
| DE | 102004040581 A1 | 3/2006 |
| WO | 9309731 A1 | 5/1993 |
| WO | 2013028990 A1 | 2/2013 |

OTHER PUBLICATIONS

Submission in response to Office Action dated Feb. 8, 2019 in EP Application No. 17720249.4.
Decision to Grant of a European Patent Pursuant to Article 97 dated Aug. 8, 2019 in EP Application No. 17720429.4.
Boshara et al., "The postoperative quality of life of the elderly following incidental durotomy during spine surgery," 65th Annual Meeting of the German Society of Neurosurgery (DGNC), pp. 1-2 (May 11-14, 2014).
Goodkin et al., "Unintended "Incidental" Durotomy During Surgery of the Lumbar Spine: Medicolegal Implications," Surg. Neurol., vol. 43, pp. 4-14 (1995).
Guerin et al., "Incidental durotomy during spine surgery: Incidence, management and complications. A Retrospective review", Injury, Int. J. care Injured, 43, pp. 397-401, 2012.
International Preliminary Report Patentability dated Jun. 6, 2018 in International Application No. PCT/EP2017/059670.
International Search Report dated Jul. 28, 2017 in International Application No. PCT/EP2017/059670.

* cited by examiner

Fig. 1
Fig. 2
Fig. 4
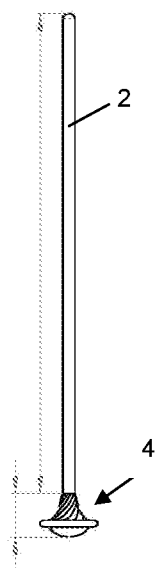
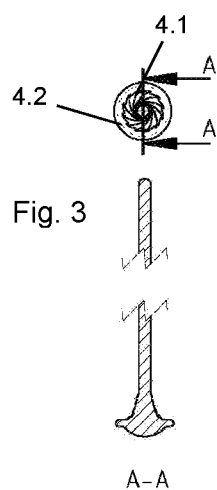
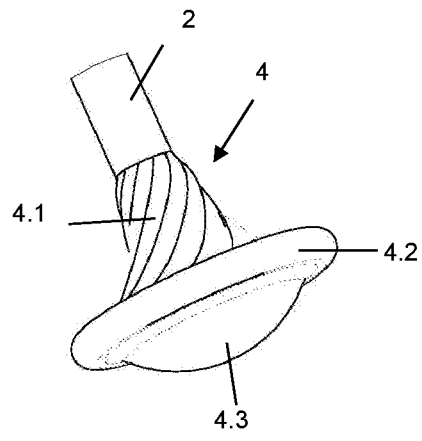
Fig. 3
A–A
Fig. 5
Fig. 6
Fig. 8
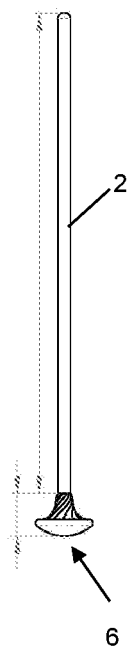
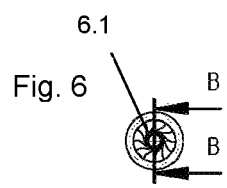
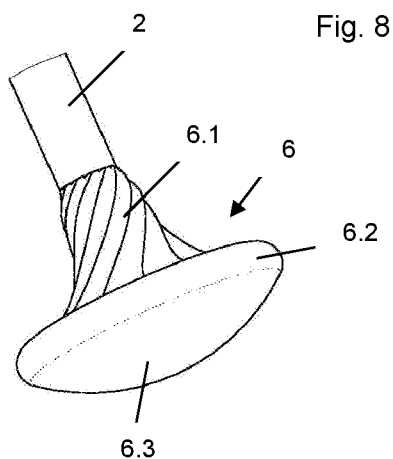
Fig. 7
B–B

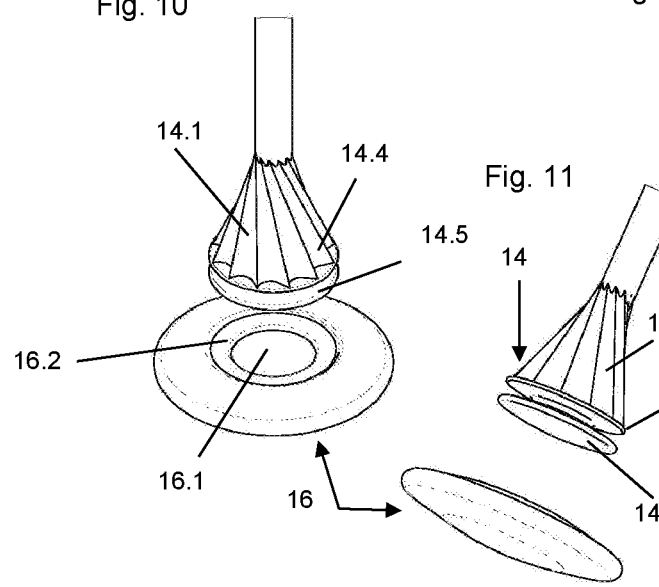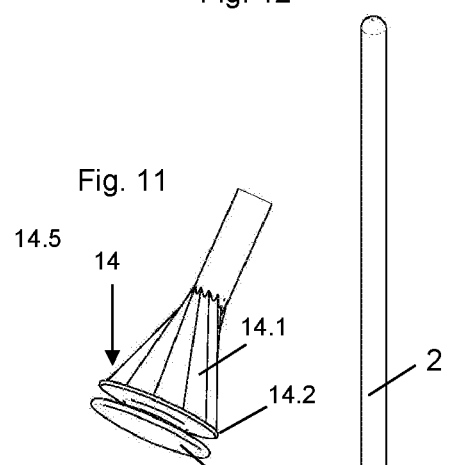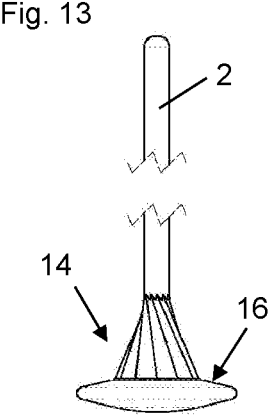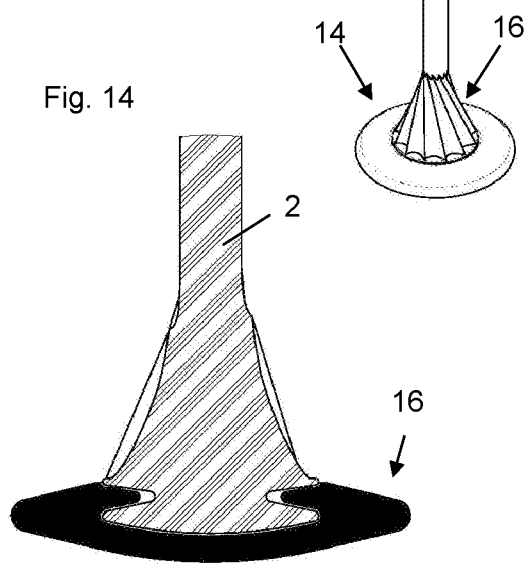

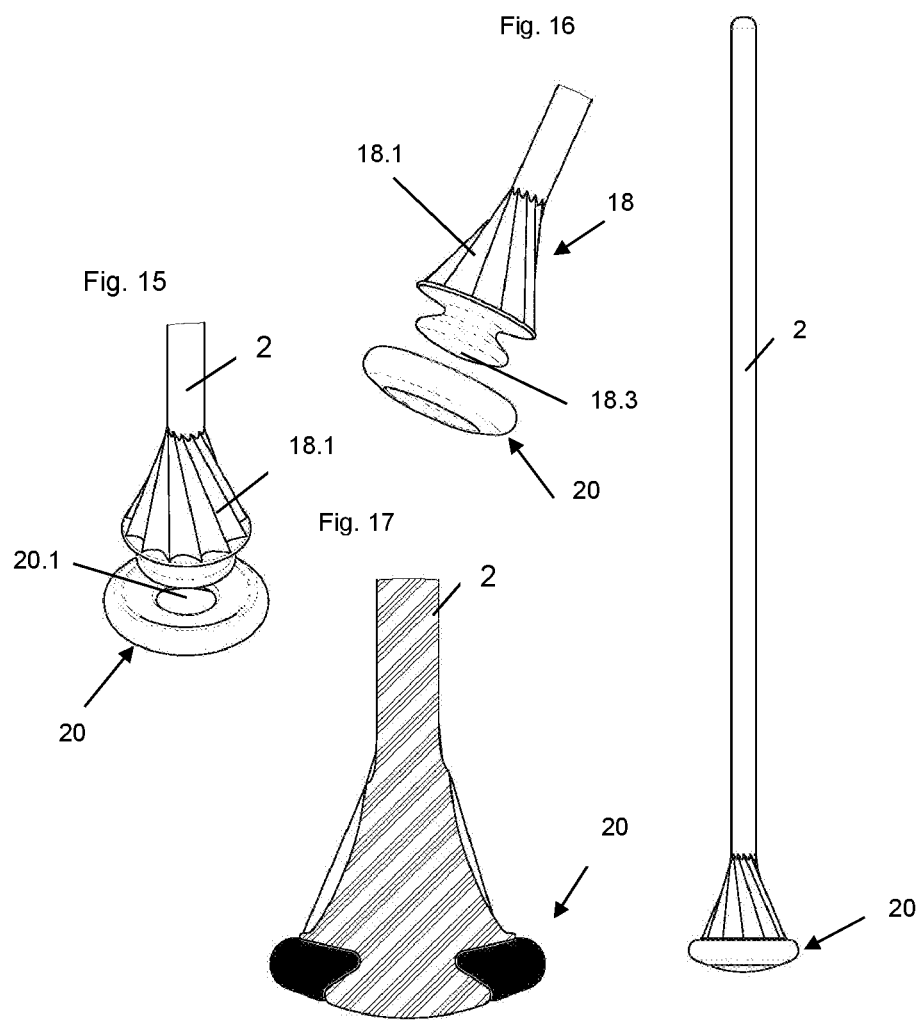

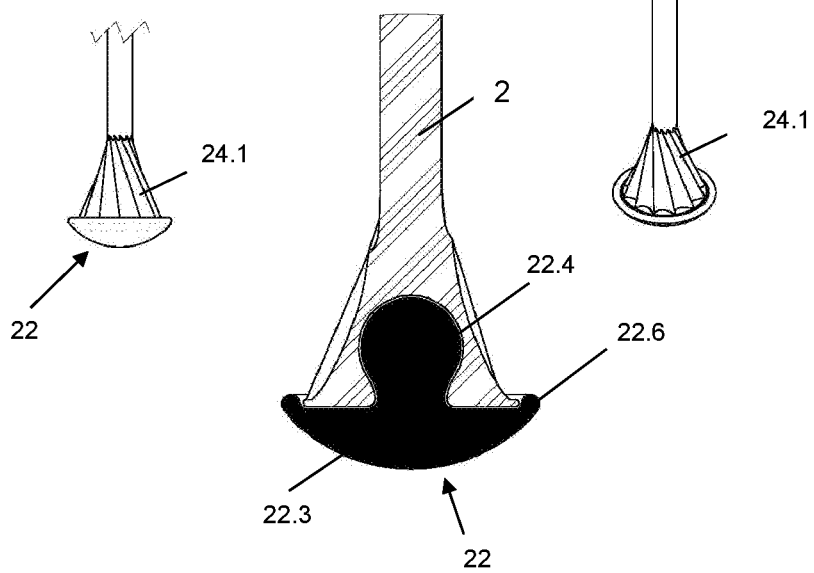

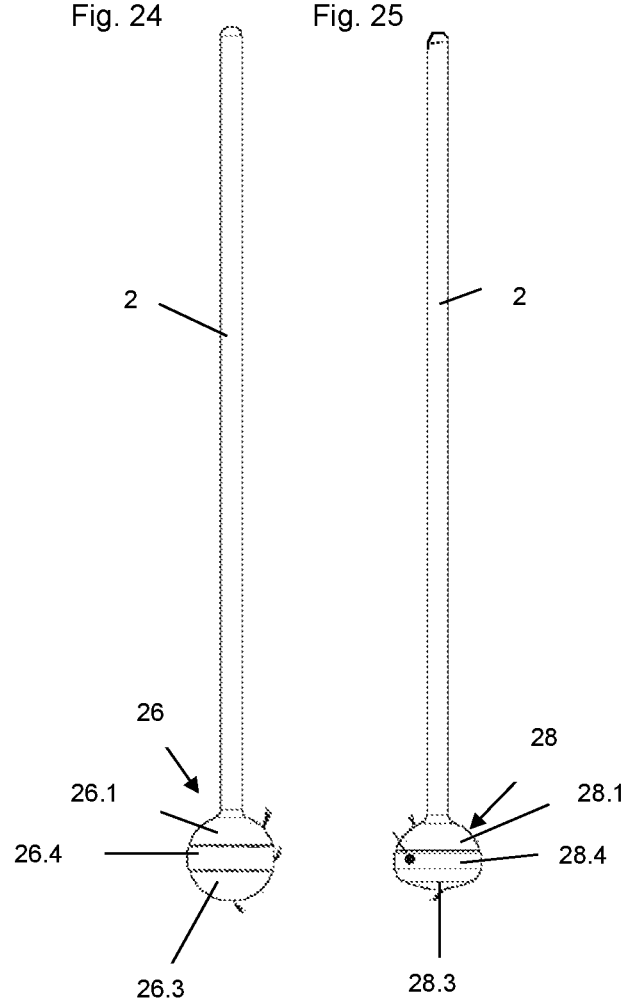

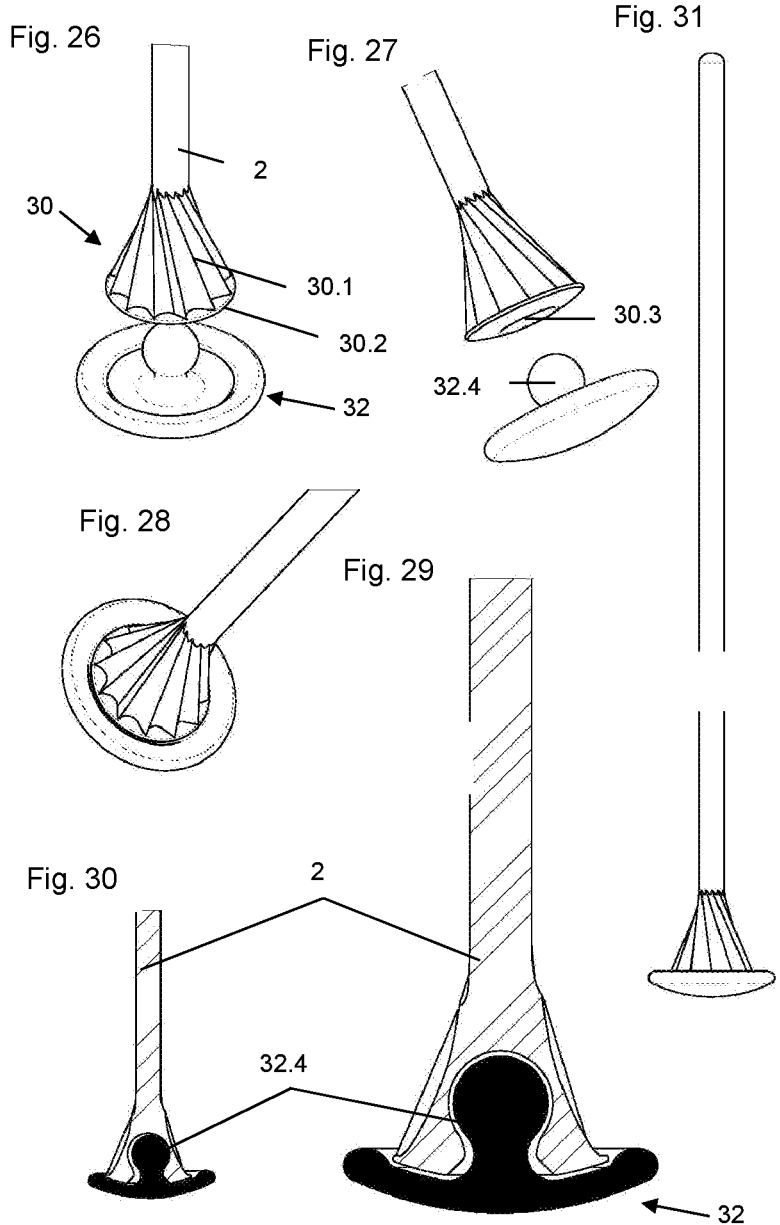

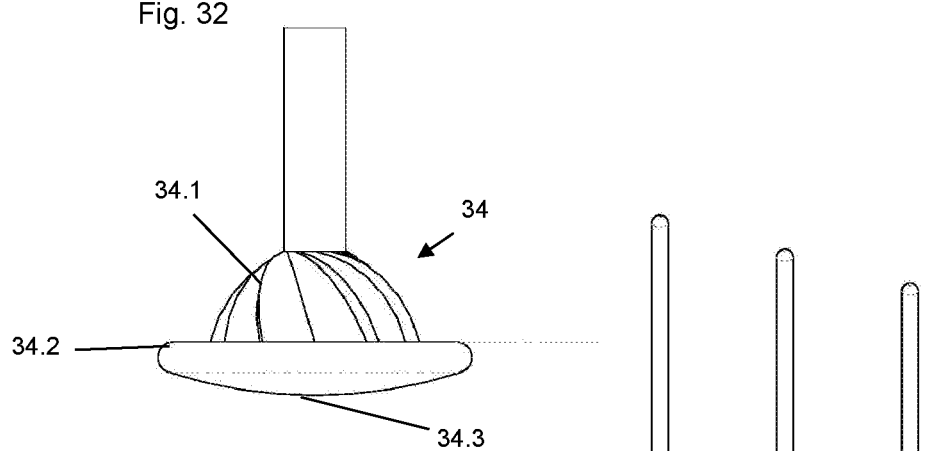
Fig. 32
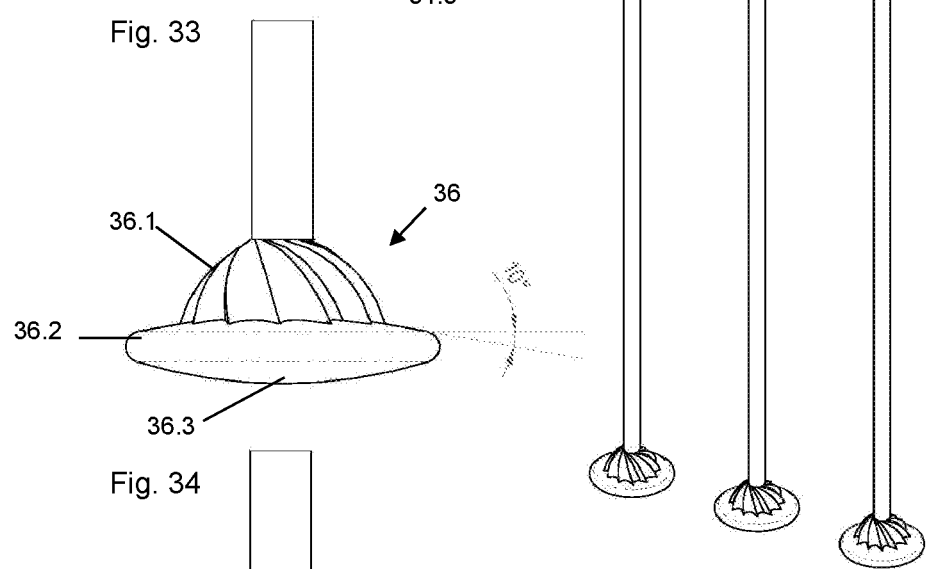
Fig. 33
Fig. 34

Fig. 35
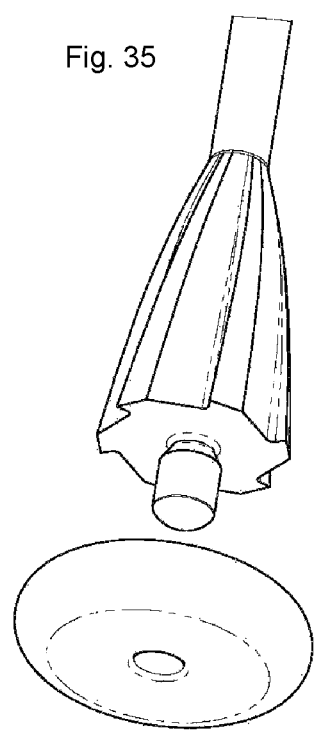
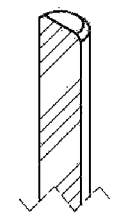
Fig. 36
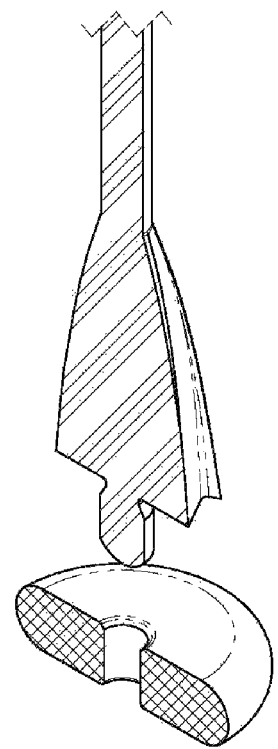

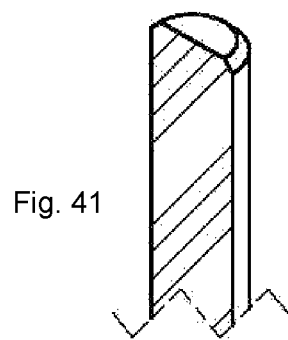
Fig. 41
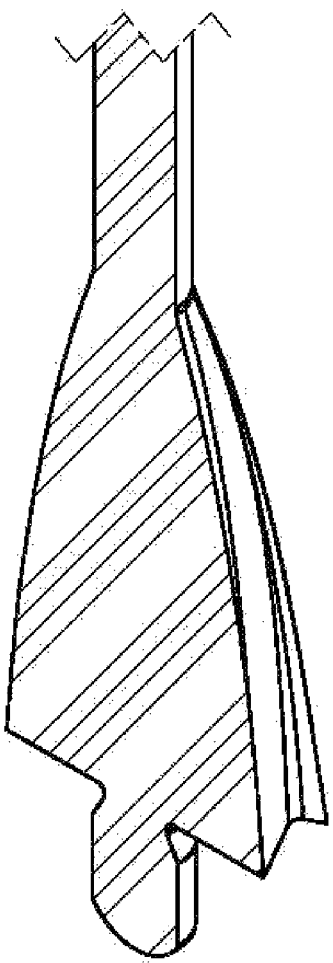
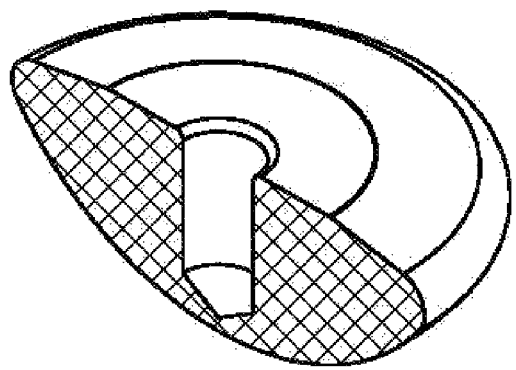

Fig. 43
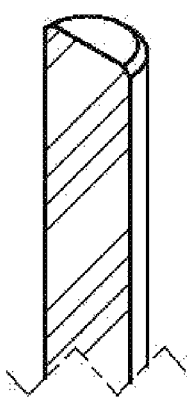
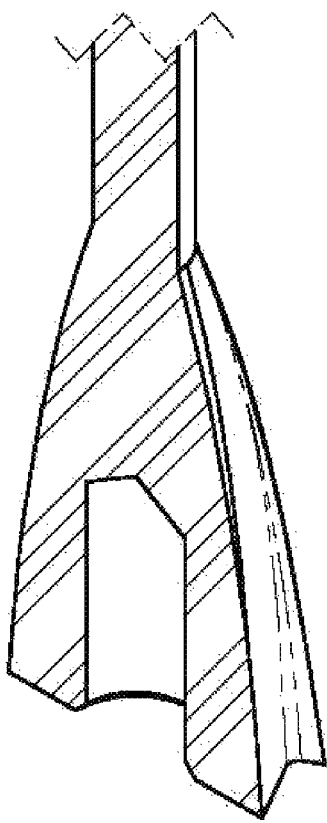
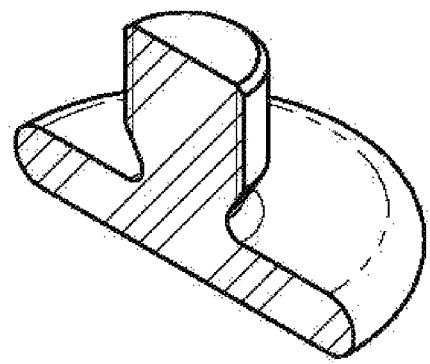

SURGICAL MILLING CUTTER

CROSS-REFERENCE TO RELATED APPLICATIONS

This application is a Section 371 of International Application No. PCT/EP2017/059670, filed Apr. 24, 2017, which was published in the German language on Oct. 26, 2017, under International Publication No. WO 2017/182673 A1, which claims priority under 35 U.S.C. § 119(b) to German Application No. 10 2016 107 549.3, filed Apr. 22, 2016, and German Application No. 20 2016 104 435.9, filed Aug. 11, 2016, the disclosures of each of which are incorporated herein by reference in their entireties.

BACKGROUND OF THE INVENTION

The invention concerns a surgical milling cutter designed for the removal of bone and/or cartilage tissue comprising a shaft which defines a longitudinal axis and which is rotatable about an axis of rotation and which has a nominal diameter and a proximal end which can be non-rotatably connected to a drive unit and a distal end opposite the proximal end, wherein provided at the distal end is a milling head having a milling surface which circumferentially surrounds the shaft and extends along the longitudinal axis of the shaft, wherein the milling surface is delimited by a proximally disposed milling surface proximal end and a distally disposed milling surface distal end and a milling surface maximum radius. The terms proximal and distal are to be interpreted in relation to the user/surgeon of the milling tool as a reference point. Proximal therefore signifies in the direction of the surgeon and distal signifies away from the surgeon.

Such arrangements can be used to perform surgical operating procedures in open, microsurgical, minimal-invasive, endoscopic or in another procedure which are employed in the context of providing access for the removal or milling away of bones, or which substantially consist of same, like for example in the case of bone decompression. Such operating procedures are carried out in particular in spinal surgery and neurosurgery but also in oral and maxillofacial surgery, ear nose and throat medicine and orthopaedics. The advantages of the invention however can also mitigate the risks of injury in further areas of application in medicine and surgery.

In many surgical interventions, in the context of providing an access, certain bone fragments have to be removed to enlarge the view into an operating area and to permit further steps in the operation. In the known operating procedure in the context of providing the access to the spinal canal the interlaminar window (narrow gap-like space between two vertebral arches=lamina) is shown after displacing autochthonic back muscle and is stepwise enlarged with milling cutters or Kerrison punches of differing sizes. In the milling operation the milling head with cutting edges that is initially selected is substituted for a diamond milling cutter to minimise the risk of injury and in particular going too deep. The process is implemented slowly, carefully, layer by layer from above downwardly as much as possible in one plane, wherein the handpiece always has to be supported with the hand guiding the milling head on the back of the patient using covering sheets. Operation is therefore effected from above downwardly or from the outside inwardly.

A particular case here is bone decompression of the spinal canal, that is to say relief in respect of the nerve roots and possibly also the spinal cord by the removal of constricting bone structures. That intervention can be either carried out as an independent operation or in the case of existing spinal canal stenosis as part of a greater intervention in the enlargement of an access in the sense of the above-described enlarged interlaminar window or hemilaminectomy, for example intervertebral disc operations or tumours as well as fusion or scoliosis operations.

Usually for bone removal purposes either bone punches or different rotating elements connected to a separate drive are used as the milling cutter. The milling surfaces of those milling cutters can be of different geometrical shapes. Substantially they all comprise a shaft which can be non-rotatably connected to a drive tool and which has a proximal end adapted for non-rotational connection to a drive tool so that the torque exerted by way of the shaft is transmitted directly to the milling head.

Existing surgical milling cutters are of such a configuration that the sharp or cutting milling surface embraces the entire milling head. Primarily spherical milling heads are used, less frequently roller-shaped, conical, pear-shaped, olive-shaped or flame-shaped milling cutters are adopted.

In known milling cutters cutting edges in the form of tooth arrangements of differing design configurations are used, or a friction surface consisting of applied crystals for example diamonds is employed. Upon rotation of the milling head and with simultaneous direct contact with the bone under pressure tangentially relative to the bone surface bone disposed therebeneath is milled or abraded away. Continuous flushing is necessary, more specifically both in order to cool the milling head which becomes hot and also to flush away the resulting bone meal from the milling head surface.

Quite often in such interventions the bone elements to be removed are directly adjacent to extremely important anatomical structures. These include inter alia: nerves, roots, vessels, cerebral and spinal cord membranes and also subjacent brain or spinal cord tissue. Injury of the above-mentioned structures by the milling surface can lead to severe damage which is not always reversible. Various complications are to be mentioned as serious consequences of such an injury, inter alia strokes, bleeding, secondary bleeding, brain neurology defects, paralysis, vision, hearing, urination, defecation, virility or sensitivity disturbances and other neurological defects and disabilities; in rare cases such complications can directly or indirectly lead to death. Injury to cerebral or spinal cord membranes "dura" (dura mater spinalis et cranialis, referred to hereinafter as "dura") and subsequent fluid discharge caused thereby (nerve and cerebrospinal fluid, brain-spinal cord fluid, cerebral fluid, liquor cerebrospinalis) usually requires direct treatment which increases the overall operating time and causes additional considerable treatment costs. That can also lead to delayed wound healing or liquor pads or liquor fistulas and consequently wound healing problems which become chronic. As a result infections can be extended in depth and for example abscesses (collections of pus under the skin) and meningitis (cerebral fluid inflammation) can occur, which have to be treated by fresh recovery operations, liquor drains and with expensive antibiotics over a long period of time.

Dura injury is the most frequent complication in spinal column operations. The selected literature set forth hereinafter explains the extent of the problems and is deemed to be for information purposes without being finally definitive.

According to the literature dura injury occurs in 1-17% of all spinal column operations, Guerin P at al, Injury, Int. J. Care Injured 43 (2012) 397-401. In a number of studies the frequency in relation to operations on the lumbar spinal column is mentioned as being at the level of about 9%, while in the case of revision interventions it occurs in 3-27% of cases.

At a presentation at DGNC 2014 incidental dura injury was denoted as the cause of moderate disability in 19.8% of cases, severe in 19% and in 12% with inability to walk and need for a wheelchair. In 30% of all cases a disability is persistent in 3 years Boshara M et al, DGN C2014, doi: 10.3205/14dgnc541.

In the United States dura injury is the second most frequent cause for actions brought against doctors by virtue of complications after spinal column operations, wherein the most frequent—Cauda-equina-syndrome—can also occur inter alia as a consequence of an intraoperative injury in milling, Goodkin et al, Surg Neurol 1995; 43:4-14.

"Between 2005 and 2013 the number of spinal column interventions in Germany increased from just 327,000 to around 750,000 by more than double". (wdrl).

In the USA 460,000 stiffening surgery operations were carried out according to AHRQ in the year 2011 alone, which according to market growth prognoses will increase by more than >5% to 2020 p.a.

In the USA too the additional costs for treatment after a dura injury were totaled up in the years 2008-2011. In that respect on average additional costs were involved at the level of $7,638 per case in relation to interventions in the region of the cervical spinal column and $2,412 per case in relation to interventions in the region of the lumbar spinal column.

These data show that this is a serious medical problem with major social and economic consequences.

Injury to one of the above-mentioned anatomical structures can occur due to minimal and extremely contact of the rapidly rotating sharp-edged milling head with one of those structures. Similar damage can also result due to the heat generated at the tip of the milling cutter by the shearing forces. To sum up: each single unskilled movement and also slipping with the rapidly rotating milling head in terms of depth (vertically) or to the side (horizontally) can have dramatic consequences. Therefore each operator must always work very carefully, with continuous flushing and only with a slight pressing force in order to avoid such events.

The conventional geometry of the milling heads with surrounding sharp-edged working surfaces does not provide protection from such unwanted injuries. The precautionary measure of applying a reduced pressing or contact force means that the removal effectiveness which can be achieved is significantly reduced so that the operations last longer.

The indicated care and the interventions which are possibly necessary, for example water-tight dura sutures nowadays prolong the operating times to a certain extent. That has medical consequences (linear increase in the infection rate as a function of time of the operation) and also economic consequences.

The literature and patent specifications both recognise the above-depicted problems and also look for a solution to the above-indicated disadvantages in the state of the art.

WO 2015/009810 proposes a specific geometry for the tooth arrangement of the milling surface. That solution can however only reduce the frequency of the above-mentioned risks in relation to short and occasional frontal contact with large-area soft parts like for example the dura mater but still cannot prevent the above-described injuries. The appropriate comparative clinical studies in regard to the actual reduction rate of dura injuries/liquor leaks are also missing. The consequences of an in particular side contact between the rotating milling head and nerve roots or vessels which are markedly more sensitive and vulnerable than the dura mater are not discussed.

DE 10 022 047 C1 discloses an instrument for cutting a calvaria, which at the distal end has a detachment body. That solution however cannot be used for all areas of application, for example it is not suitable for the spine. The sharp working surface here ends in front of the detachment body. The milling cutter which tapers conically towards the tip is perhaps geometrically suitable for point or radially implemented, narrow interventions or cuts—but not for the more complicated use at the spinal column because much more bone tissue has to be removed in such operations. In particular the basic problem of slipping off is not resolved with that device, which is problematical in particular in relation to a dural sac which is filled with neural fluid as that is under a constant pressure of 0-15 mmHg (0-2 kPa). Compression with the protection arrangement affords both a minimal increase in pressure and also reactive warping of the dural sac—also in proximal relationship with the proximal contact surface of the protection arrangement in the direction of the axis of rotation and the rotating working part.

The rotating instruments used hitherto—drills, milling cutters and milling heads—do not satisfactorily avoid the above-depicted disadvantages.

There are admittedly some special milling heads with a blunt or a smooth end surface or cup, for example nail milling cutters for diabetics from various manufacturers, some dental and endodontic drills, a radius milling cutter from Metabowerke GmbH or an osteophyte milling cutter from Aesculap AG. The geometries used reduce the risk of injury only inadequately if at all.

In particular those devices do not afford protection from injury in the event of inclined and only slightly tilted contact, that is to say which is not strictly tangential or even lateral, with the soft anatomical structures. Those devices can even give the operator a false sense of security and thus encourage risky behaviour.

Technical Problem (Object)

The technical problem (object) of the invention is to at least partially overcome the above-depicted disadvantages and in particular to provide a surgical milling cutter and thus to reduce or entirely eliminate the many unwanted injuries in the case of medical interventions.

BRIEF SUMMARY OF THE INVENTION

To resolve those problems the invention proposes the atraumatic configuration of the motor-drivable milling cutter, which means that the milling cutter is of a tissue-conserving configuration and does not cause injury. In the most abstract embodiment this is achieved in that it is of an atraumatic configuration, the milling surface is also proximally operative, the milling surface is enlarged in the distal direction radially beyond the nominal diameter of the shaft, that a protective arrangement is provided at the distal end, the protective arrangement is provided distally from the milling surface distal end, the protective arrangement has a distal contact surface and a protective arrangement maximum radius for forming a protective ring which surrounds the milling surface maximum radius or the milling surface maximum periphery defined thereby in an annular configuration so that upon rotation of the milling cutter the protective arrangement defines around the milling surface a circumferentially surrounding protective zone extending from the protective arrangement maximum radius to the milling surface distal end.

This protective arrangement which is arranged distally from the milling surface on the milling cutter shields the tissue items which are below (distally) and laterally (radially) of the milling surface, for example dura, nerve root, and vessels, from the sharp-edged and only proximally acting milling surface. By virtue of suitable establishment of the variable dimensions of all parts of the milling head the protective arrangement is established with the safety margins relative to the adjacent soft parts and the anatomically required possible options as well as handling.

According to the invention the milling surface is also adapted to act proximally, which means that it is adapted to mill or cut in the proximal direction, which does not exclude the point that it can also be used for radial cuts. By virtue of that design configuration for the first time a pull can be exerted on the shaft.

The protective zone is a virtual space generated in operation upon rotation of the milling cutter, in the sense of a rotational body which is proximally delimited by the proximal end of the milling surface (milling surface proximal end) and distally by the protective ring and its protective arrangement maximum radius R2 which annularly surrounds the milling surface maximum radius R1, that is to say the maximum radial extent of the milling surface from the axis of rotation.

Development of the invention is based on the realisation that a specific geometrical configuration, appropriate to the needs involved, of the protective ring, means that there is no risk of injury by penetrating tissue in proximal relationship with the protective ring in routine operations and tilting of the milling cutter is made possible. Tests have shown that the protective arrangement maximum radius R2 should be at least the magnitude of the milling surface maximum radius R1 plus the tolerance plus ten times the concentricity, but it can also be markedly larger. In contrast a zone around the milling cutter which goes at the inside from the respective radius of the milling cutter, that is provided in the direction of the longitudinal extent, plus the upper limit deviation plus the concentricity, has proven to be unsafe.

The specific geometrical configuration of the protective arrangement can be adapted in accordance with the respective needs involved, that is to say the size, length and width or periphery and degree of convexity of the protective arrangement and the distal or radial safety spacing implemented thereby in relation to the adjoining soft tissue parts, which are disposed in front of the distal contact surface and around the distal contact surface of the protective arrangement.

The protective ring surrounds the milling surface maximum periphery in an annular peripheral configuration and thus forms the region of the maximum radial extent or the region of the maximum periphery and thus keeps the surrounding tissue away from the milling surface.

The minimum size of the protective arrangement maximum radius R2 min is as follows:

$$R2\min = \frac{L \times K}{\tan\beta 1} - \frac{r - r \times \tan\beta 1}{\tan\beta 1} + R1 + T + 10 \times RO$$

The meanings therein are as follows:
R2 min: minimum protective arrangement maximum radius L: length of the protective arrangement along the axis of rotation K: coefficient of the purposive geometry of the protective arrangement $\beta_1$: wedge angle of the proximal wedge surface or contact surface of the protective arrangement r: radius of the radially outer rounded configuration of the protective arrangement R1: milling surface maximum radius of the milling cutter T: upper predetermined limit deviation RO: predetermined concentricity value $\beta_1$, L, r and R1 are measured in the longitudinal cross-sectional plane (along the axis of rotation) of the milling cutter. T and RO are determined for the specific production process from the general standards (DIN, EN, ISO and ANSI) or company standards. The coefficient of the purposive geometry (K) is calculated by the purpose of the product (technical documentation) and from the scientific data (anatomy).

Thus there is the possibility of working out the individual values and selecting a suitable milling cutter for a specific situation of use (for a given intervention for a given patient on the basis of his imaging). The value R2 min calculated on the basis of that formula thus provides a minimum protective arrangement maximum radius which reduces the risk of dura injury to below 0.01%, so that this is out of the question for all practical cases.

The protective arrangement which is smooth and therefore edge-free forms at the distal end of the milling cutter the distal contact surface and with the protective arrangement maximum radius provides a protective arrangement maximum periphery which surrounds or embraces the maximum periphery of the milling surface at the outside in the form of a protective ring, that is to say of an annular configuration, being therefore in the form of a closed transition-less circular ring. Depending on the situation of use the length of the protective ring in the longitudinal direction of extent of the milling cutter is preferably between 0.25 and 4.5 mm, wherein a length of 1 to 4 mm in relation to operations on the lumbar spinal column and a length of 0.5 to 2.5 mm in relation to operations on the cervical spinal column have been found to be appropriate. A length of between 0.25 and 2.5 mm is particularly suitable for interventions at the base of the skull, in ENT surgery (middle ear operations) and in relation to oral and maxillofacial interventions.

The length L of the protective arrangement is restricted by the anatomical conditions. The epidural space extends between bone and dura. That is a hollow gap-shaped space under the bones in which the protective arrangement of the milling cutter can be safely introduced without the dura by mistake being compressed and damaged. In the region of the cervical spinal column that gap is centrally even 2 to 9 mm, laterally the gap is substantially narrower—depending on the height it is only 0.8 to 2.5 mm. In the case of spinal canal stenosis it is even still less.

The distance between the nerve root and the bone is 1.9 to 4.1 mm above the root. The root can be further gently displaced more deeply by 1.5 to 3.1 mm with the protective arrangement of the milling cutter in the root canal.

The length L of the protective arrangement is to be adapted on the basis of those values or calculated from the pre-operative patient imaging. The appropriate maximum values L are in the ranges set out below:

| | |
|---|---|
| Cervical spinal column | 2.5 mm |
| Thoracic spinal column | 3 mm |
| Lumbar spinal column | 4.5 mm |

The distal contact surface of the protective arrangement thus forms—at least partially—the contact surface of the milling cutter in the vertical direction and the protective arrangement maximum periphery determines the lateral and therefore horizontal protective space around the milling surface. When milling between the sharp milling surface and the anatomical structures which adjoin same laterally (horizontally) and below, that is to say distally or (vertically) from the milling surface, the protective arrangement forms a virtual three-dimensional safety zone which keeps the tissue surrounding the operating region away from the cutting surface and thus effectively prevents unwanted injury to that tissue, but at the same time permits unrestricted removal effectiveness with good handling. The protective arrangement thus for the first time affords horizontal and also vertical protection for the surrounding tissue.

The protective arrangement is disposed around the milling surface at the front distal end, that arrangement preventing contact with the delicate tissue—irrespective of where it is to be found—both vertically and therefore under the protective zone and also horizontally and therefore beside same (at the perimeter).

As it is possible to operate with the proposed milling cutter differently from hitherto, even when slipping occurs unintended injury depthwise is effectively avoided. In contrast to known operating procedures when using the milling cutter according to the invention the milling cutter is bit by bit pulled tangentially out relative to the bone edge and not pressed in. Accordingly the resultant force is always tangential relative to the bone, that is to say laterally and rather rearwardly, being therefore proximally outwardly from the operating area, that is to say in the direction of the handpiece.

As there are as good as no structures to be injured when pulling the cutter out the milling cutter can be used with markedly more force than in known operating procedures. That considerably reduces the operating time. As the protective arrangement provides for self-centring of the milling cutter the risk of unwanted slipping is eliminated. In that respect there is no limitation in terms of the application of force and it is possible to employ the sub-maximum permissible pressing force tangentially with respect to the bone edge (approximately perpendicularly (+/−30 degrees) relative to the longitudinal axis). Sub-maximum is to be interpreted in the sense of fingertip feel so that a piece of bone cannot be fractured or broken off by the application of force itself. The subjective bone density which is felt varies between "rock-hard" and "plasticine-like" depending on the patient. In the case of pronounced osteoporosis that requires very delicate handling.

The milling cutter according to the invention makes it possible to operate with almost three times the application of force, this entailing approximately the same improvement in cutting efficiency, cutting force and cutting speed. The level of the applied force can be compared by the surgeon as between known milling cutters and the milling cutter according to the invention by means of a dynamometer. Hitherto a surgeon was able to operate in relation to a surface with a force of a maximum of 30N, but that applied force then had to be reduced to 5 Newtons for safety reasons. In contrast with the milling cutter according to the invention the surgeon can operate continuously with a force of up to 80N, more specifically irrespective of depth. The protective arrangement is preferably designed to enlarge the distal contact surface and/or the protective arrangement maximum periphery of the milling head, by between 1.5 and 3 times in certain embodiments. With the removal effectiveness maintained this configuration provides that all soft tissue pieces which are disposed distally of and beside the milling head are protected and treated carefully, more specifically without limitation in terms of freedom of movement for the operator in the milling process or in the operation.

In the milling operation the protective arrangement at all usual working angles provides protection from the above-described unintended injuries to the tissue surrounding the operating area, which basically are dependent on the kind of kind of intervention, the access route and the individual anatomical conditions, for example the thickness of the fat layer, the variable configuration of the vessels and nerves and so forth. Thus for example it is possible to operate for example at the spinal column with a dorsal access of a maximum −45 degrees medially to a maximum 90 degrees laterally and a maximum −90 degrees to a maximum 90 degrees in the cranio-caudal plane.

A preferably smooth or polished-smooth configuration of the protective arrangement at the distal end of the milling cutter provides protection in the case of occasional or prolonged contact in the milling operation for the particularly endangered delicate structures from injury and also permits safe and substantially quicker implementation of the intervention.

By virtue of the smooth protective arrangement the milling cutter can also be introduced into the tissue or between bones gently and without the risk of injury and the surrounding tissue can be pushed aside therewith. That is welcome in particular in a modern minimum-invasive procedure because the above-mentioned structural features mean that a lower pressure has to be exerted in respect of the skin opening and also the tissue damage caused by the access. That expedites wound healing and reduces the frequency of wound healing disturbances and other infectious complications. The minimum-invasive operating procedure makes it possible for the patient to be early mobilised post-operatively (as a consequence thereof the risk of thromboses/embolisms and lung inflammation is reduced), post-operative pain is less severely pronounced so that fewer pain killers also have to be administered.

The maximum diameter of the protective arrangement and thus the maximum periphery thereof determine the lateral safety spacing and the possible curving of the tissue from the side. The above-mentioned dural sac which is filled with spinal fluid is admittedly also compressed by the protective arrangement, but damage becomes substantially less probable by virtue of the reduced surface pressure produced by the protective arrangement so that the dural sac can even curve proximally from the protective ring to the protective arrangement without damage.

In the case of flat operations, directed therefore only in the horizontal direction or sideways, that is to say without a change in the depth of penetration, the protective arrangement also acts in that respect in centring or positioning relationship because the milling cutter is guided by same at the surrounding bones. The rounded edge of the protective arrangement in that case always provides protection from injury in relation to lateral contact.

The following advantages are achieved by the invention:
  The intended bone surface is exclusively and specifically milled away.

All tissue structures in front of and beside the milling head are treated carefully by the protective arrangement.

With sufficient flushing for the purposes of cooling and lubricating this permits occasional or continuous contact with the vulnerable surrounding tissue in the milling operation.

By virtue of the smooth protective arrangement the anatomical structures are pushed aside and/or kept away gently.

The milling cutter is always held in the target position by the edge-free protective arrangement, in particular by the protective ring, and it is therefore of a self-centring configuration, whereby neither slipping or vertical penetration in terms of depth can occur. The protective ring improves maintaining a spacing in relation to the surrounding tissue.

Therefore without an increase in risk of intraoperative injury it is possible to use a pressing or feed force which is up to three times higher, in which respect the temperature rises more slowly upon an increase in the applied force; sufficient cooling and lubricating flushing, preferably with a saline solution, is presupposed.

For the first time that permits a removal efficiency which is up to three times higher in the milling operation, this reducing the duration of an intervention.

Although this admittedly depends greatly on the operator and the individual case in question, in most cases time savings of 25 to 50 percent and more were achieved, so that the average operating time of about 45 to 60 minutes was reduced to about 15 to 25 minutes.

By virtue of the smooth protective arrangement having rounded edges, which distally surrounds the milling surface, the milling cutter can be guided directly parallel to the bone edge to be milled away along the location of use at the bone edge so that it is possible to use milling head diameters which are markedly larger than hitherto usual. That permits a removal efficiency which is up to three times higher and thus reduces the duration of the operation. Because of the higher thermal capacity of the larger milling cutter with the consequently larger protective arrangement the temperature in the milling operation rises markedly more slowly than with conventional milling cutters.

The protective ring thus also forms a proximal contact surface which is preferably of a plate-shaped configuration and permits gentle guidance of the milling cutter along a bone edge to be processed. The proximal side of the protective arrangement or of the protective ring can therefore come into contact with the bone edge or the bone surface for guidance purposes and in so doing is supported against the bone edge.

To increase the size of that contact surface the protective arrangement can include an atraumatic intermediate portion between the milling surface maximum radius and the protective arrangement maximum radius which can be of any desired configuration according to the needs involved, for example it can be in the form of a straight, convexly or concavely curved surface or also in the form of a free form surface.

Embodiments provide a relative displacement between the axis of rotation of the milling cutter (milling cutter rotational axis) and an axis of symmetry of the protective arrangement, which however is then not non-rotatably connected to the milling cutter, thereby providing for improved adaptability in particular in tight anatomical conditions.

To provide a particularly large protective arrangement with a particularly long lever arm and a good protective action the mushroom-shaped configuration of the distal contact surface has proven to be particularly desirable. Mushroom-shaped means that both convex or straight surfaces of the protective arrangement are of a similar shape to the cap of a mushroom and form a peripheral wedge portion having a rounded tip—either by the virtual prolongation lines of the surfaces themselves or by way of the tangents to both surfaces which are preferably convexly curved.

Besides the protective arrangement being in the form of a protective ring which initially only atraumatically involves the maximum periphery of the milling surface a configuration in the form of a protective cap is however also possible, which beside the maximum periphery also atraumatically surrounds the distal end. That protective cap surrounds the distal end as far as the maximum periphery at the front side of the milling surface, and therefore involves or surrounds the front distal end at least cap-like as far as the milling surface maximum radial periphery.

The protective cap preferably has a positive degree of convexity and is therefore of a spherical configuration, it can however also be centrally flat or concave. The distal surface of the protective cap thus forms the distal contact surface of the milling cutter. The distal contact surface of the protective arrangement is thus slightly cushioned at the tissue and therefore besides the distal contact surface forms a slightly elastic second support point with the tissue, which additionally stabilises the milling cutter and has a vibration-damping action.

In the preferred convex configuration therefore the protective cap forms the distal contact surface having the configuration of a segment of a ball. For the surrounding tissue that affords predominantly vertical and therefore front-side protection, but also horizontal protection, when the milling head is oriented inclinedly. In that way all tactile structures arranged in distal relationship with the protective arrangement are treated carefully, even if direct frontal contact occurs for a prolonged period; with sufficient flushing, cooling and lubrication, even permanently.

In order to gently push the tactile soft tissue pieces away from the piece of bone to be milled away and to permit good bonding in relation to the bone surface a configuration of that protective cap, in the shape of a segment of a ball or of a mushroom configuration, has proven to be particularly desirable.

An improvement in the protective action can be achieved by the provision of a protective zone which surrounds the surface of the milling cutter also above the milling surface maximum radius in a girdle-like configuration. That protective girdle can be of differing configurations, thus for example in the form of a narrow, smooth or coated outer peripheral girdle which effectively protects the soft tissue pieces from lateral contact with the milling surface.

The milling surface preferably merges into the protective girdle without a transition or at any event without an edge, the girdle extending proximally from the milling surface maximum radius, preferably by 5 to 10 percent.

In that arrangement the protective girdle is of a slightly larger radial extent than the milling surface maximum radius of the milling cutter at the end of the milling surface so that it girdle-like surrounds the lower distal end of the milling surface. The protective girdle which is of a flat and edge-less configuration therefore surrounds the maximum periphery of the milling surface and thus forms a protective girdle or ring which peripherally surrounds the maximum periphery.

The radius or curvature of the protective cap can be smaller or larger than the radius of the milling surface maximum periphery, adapted to the situation of use. Preferably the protective cap is in the shape of a segment of a ball but can also be of a complex geometry or a non-spherical geometry. A smaller configuration makes it easier to penetrate under the bone edge whereas a larger configuration increases the safety space defined by pushing away the surrounding tissue. A preferred configuration is one in which the radius of the protective cap is markedly larger than the radius of the maximum periphery, preferably it is about 5 to 10% greater than the milling surface maximum radius or periphery. In that way in the preferred embodiment the protective cap forms a distally projecting, mushroom-shaped surface formed by a segment of a ball, which distally extends at least from the milling surface maximum periphery to a distal front end and includes a distal contact surface.

The protective action of the protective arrangement can also be improved by a reduced-resistance configuration. In that case the protective arrangement can consist entirely of such a material, for example PTFE/Teflon® or can also be only partially coated with same so that the protective arrangement represents a minimum resistance. Preferably that is implemented by smoothing or polishing. A ceramic, metallic or plastic-containing coating (for example PTFE//Teflon®) on the protective arrangement is also possible, in which respect however it is to be noted that the milling surface is not coated.

The design and configuration of the sharp-edged milling surface which is in the form of a rotational body as well as the kinds of tooth arrangement can be selected as required. It can be for example in the form of a hemisphere or conical or spindle-shaped, in which respect any convex or concave variants are also possible as well as special shapes (for example hourglass-shaped). Preferably the milling surface includes cutting edges which extend parallel or inclinedly relative to the longitudinal axis of the milling head on the milling surface. The milling surface can also include helical or straight grooves and it is possible to provide rake angles which permit friction-less cutting of corticalis bones, wherein those angles are usually positive and are generally about 5° to 15°, particularly preferably 7°. With a clearance angle of preferably 15° that provides a wedge angle for the cutting edge of about 60-70°. In a further embodiment small crystals (for example corundum, zirconium, diamond) are applied to the milling surface using different methods.

The twist angle of the milling surface is preferably in the range between 0°-35°. For interventions at the vertebrae a left-hand twist angle of preferably 15° has proven to be particularly desirable to achieve optimum removal.

The proposed milling cutter can also be used in other technical fields, more specifically in all areas of use in which on the one hand operation must be effected with a sharp milling cutter but at the same time structures disposed in the vicinity of the milling head must be treated carefully. Besides human medicine this can also be used in dentistry but also in veterinary medicine. Other areas of use in other technical fields are also possible, for example in mechanical engineering, in jewelry making, in model making, in chiropody and the like.

The distally arranged surface of the protective arrangement is smooth, which is preferably effected by polishing. It is further desirable if edges are rounded off and the lower distal end of the milling surface ends proximally from the lateral edge of the protective girdle.

In the preferred embodiment at least the milling head of the milling cutter comprises steel, a steel alloy, carbide, plastic, ceramic or suitable combinations of those materials.

The milling cutter is in particular in the form of a rotational member, wherein in the production thereof from a solid material, firstly the distal protective arrangement is turned, then in the distal direction a cone is implemented in the region of the cutting surface and finally the cutting surface is produced on that cone.

Preferably the radial spacing of the milling surface increases from the proximal end (milling surface proximal end) to the distal end of the milling surface (milling surface distal end), wherein any desired configurations of the milling surface are possible, adapted to the respective situation of use, in particular a surface configuration rising progressively to the distal end or however also a complex surface configuration. That proximally operative configuration of the milling surface for the first time permits milling/cutting in a proximal direction. That is implemented in particular by a configuration of the milling surface, that enlarges conically distally in the direction of the longitudinal extent, for example by means of a conical milling head which enlarges from the milling surface proximal end to a milling surface distal end in a conical configuration and the peripheral surface of the milling surface includes a profile angle σ of less than 90 degrees with a plane extending transversely relative to a longitudinal axis. The conicity does not have to involve the same gradient at every location, but the invention permits any desired configurations of a distally enlarging, rotationally symmetrical milling head. Rather, in accordance with the invention, a concave or convex configuration of the milling surface which enlarges radially in the distal direction can also be implemented, adapted to the respective situation of use. It is precisely that enlarging configuration of the milling surface which makes it possible to mill the bone away so-to-speak in withdrawal relationship by virtue of the proximally directed mode of operation.

In addition a larger area of the bone can be milled by tilting the milling cutter.

That for the first time permits "undercutting", which means that more bone is removed from the distal bone layer than from the proximal bone layer and at least a thin boney bridge can remain at the proximal bone surface.

In additional the milling cutter can be tilted and moved while resting on the distal contact surface of the protective arrangement, in which case movement away from the former axis of rotation of the shaft to the respective point of the milling surface that is in contact with the bone acts as a lever arm to increase the force involved. In that way, to achieve the desired forward movement, the surgeon has to apply markedly less force of his own, which is advantageous in particular in the case of long and complicated operations and reduces fatigue on the part of the surgeon. In summary therefore the surgeon has to apply less force but at the same time can operate with a greater feed movement.

A fluctuating pressing force between the milling surface and the bone has proven to be particularly desirable for the milling operation because that promotes transporting the removed bonemeal away and flushing it out. In addition, by virtue of the gap periodically occurring due to the movement visual checking is considerably improved for the surgeon. In addition a vibration produced by fluctuating loading of the working surface helps to step-wise push the conical protective arrangement under the bone.

Besides milling heads which are made in one piece and preferably from metal a two-part configuration is also in accordance with the invention. In that case the entire protective arrangement including the protective ring and the protective cap can be adapted to be connected to the distal contact surface or only the protective ring can be connected to the milling cutter, whereby the milling cutter then has the distal contact surface. In the case of a protective ring which can be connected to the milling cutter a configuration in the form of a toroidal protective ring has proven to be particularly desirable.

In the two-part configuration the milling head with the cutting surface is preferably made from metal, in particular in the form of a turned member, and the protective arrangement which can be connected to the milling head can comprise another material.

The protective arrangement which is thus interchangeable can in that respect be produced separately and for example using an injection moulding process.

Various technical options for making the connection between the milling head and the protective arrangement are possible. In the preferred embodiment a seat for the protective arrangement is provided on the milling head in particular distally from the milling surface with the maximum periphery thereof, the seat for example being in the form of a groove or an undercut portion.

An embodiment for fixing the protective arrangement to the distal end of the milling head includes a screw connection. In that respect basically two different configurations are possible, namely a male version and a female version. At the distal end beneath the milling surface the male version includes a threaded pin which can either be connected directly to the protective arrangement or which can be connected by means of an additional nut which is received in a receiver of complementary configuration in the protective arrangement in such a way that in the operation no edges can come into contact with the surrounding tissue. In contrast the female version in the distal end of the milling head includes a female thread into which a fixing element holding the protective arrangement, for example a threaded pin having a hexagonal socket, can be screwed.

The screw thread pairing is preferably such that upon rotation of the milling cutter about the axis of rotation, it causes tightening of the threaded connection. In that way the torques occurring upon use actively contribute to securing the arrangement and prevent the protective arrangement from coming loose or twisting off the milling head.

The advantage of the separate design configuration of the protective arrangement from the milling cutter lies in the better sterilisation options and re-usability. Thus the protective arrangement can be made from a plastic material which can be used only once or only several times, whereas the milling cutter with the milling head is preferably made from high-quality steel which can be sterilised or re-sterilised. It has further been found that complex geometrical configurations of the milling head with milling cutters and grinding discs are easier to manufacture if the protective arrangement is subsequently secured to the milling head.

The protective arrangement, whether it is now in one piece with the milling head or whether it is in the form of a protective attachment which can be connected to the milling cutter, can be of a design adapted to the situation of use, for example in the form of a spherical segment of a ball, a ring, a partially flattened ball, a toroidal ring, a disc, or a disc with a concavely curved protective surface at the distal front end.

The protective arrangement can thus include portions involving a number of geometries or different geometry portions for performing different functions. A first portion includes the protective ring which possibly only surrounds the milling surface maximum radius or additionally distally shields same. A second portion can involve a portion of smaller radial extent in relation to the first portion, for example that second portion can include the protective cap, preferably in the form of a closed hemispherical segment extending distally from the first portion with the protective ring, or also in the form of an annular protective collar which at the outside also involves the geometry of a hemispherical segment.

The disc-shaped configuration of the protective ring has also proven to be desirable, which decreases from the milling surface maximum radius radially outwardly, preferably continuously, in respect of length, and thus forms a disc or wedge around or distally from the milling surface maximum radius at the outer peripheral edge.

A configuration of the protective ring which is inclined at least at one side and preferably at both sides and which is thus wedge-shaped, at least at the outer radial edge, has proven to be particularly advantageous because that simplifies the operation of pushing away the surrounding tissue without injury. In that case the inclined portion causes the force applied axially along the longitudinal axis of the wedge configuration, that is to say transversely to the axis of rotation of the milling cutter, to be broken down into at least one normal force acting on the tissue from the inclined surface or, in the preferred configuration, normal forces applied by both wedge surfaces.

The inclined configuration or the radially outwardly extending reduction can begin directly adjoining the milling surface maximum radius, which include an initially non-reducing intermediate portion between the milling surface maximum radius and the conical or reducing radial outer edge of the protective ring.

Embodiments provide identical or different proximal wedge angles $\beta_1$ and distal wedge angles $\beta_2$. The proximal wedge angle $\beta_1$ is the angle included between a transverse line extending transversely relative to the direction of the longitudinal extent (axis of rotation) through the centre of the protective ring and a prolongation of the proximal surface of the protective ring or a tangent to that surface, and the distal wedge angle $\beta_2$ is the angle included between the transverse line and a prolongation of the distal surface of the protective ring or a tangent to that surface. The proximal and distal surfaces of the wedge-shaped protective ring can therefore be flat and curved (convex, concave or in the form of a free form surface). The wedge surface can extend either from the milling surface maximum radius to the front rounded configuration or it can include a further intermediate portion of any desired configuration.

In the development of the invention, wedge angles of:

$$1.5° \leq \beta_1 \leq 45°$$

and $$-35° \leq \beta_2 \leq 45°$$

has proven to be particularly advantageous.

Furthermore in development of the invention it was found that the angle $\beta_2$ is determined by the anatomy of the patient. More specifically the bone surface determines the appropriate angle. In the case of pathological constriction of the spinal canal (spinal canal stenosis), an indication of operative treatment, the angles have to be appropriately adapted. In the case of interventions at the spinal column the anatomical conditions and resulting proximal angles $\beta_1$ are as follows:

| Operating area | $\beta_1$ |
| --- | --- |
| Cervical spinal column dorsal | 20° |
| Thoracic spinal column dorsal | 17.5° |
| Lumbar spinal column dorsal | 29° |

| Operating area | $\beta_1$ |
|---|---|
| (without spinal canal stenosis) Lumbar spinal column dorsal (with spinal canal stenosis) | 25° |

Because of slight anatomical differences at any level and anatomical variety (normal variations between healthy humans) a respectively symmetrical tolerance of ±15 degrees can occur.

The invention for the first time affords the option of individually determining that angle $\beta_1$ for each patient on the basis of indication of the symptoms by means of imaging (for example computer tomography) and thus using the "appropriate" protective arrangement individualized for the planned intervention. That is extremely useful for example in the case of deformities like scoliosis or kyphosis operations. In those very complex and arduous operations with attendant risks osteotomy (bone removal) is the appropriate operating procedure. In that operating procedure the operator deliberately severs bones extensively in order to align the spinal column (serial laminectomy operations). In a pedicle subtraction osteotomy (closed wedge osteotomy) in contrast the lower part of the spine is removed so that it can be tilted rearwardly. In the spinal column resection one or more complete vertebrae is removed through a rear access to the spinal column. Dorsal osteotomy (also referred to as "Smith-Peterson" or "Ponte" osteotomy) signifies removal of the vertebral arches together with facet joints and the interspinous ligaments. That is also the case in ventrodorsal osteotomy (from the front and from behind) and spinal column resection (from the dorsal).

If the proximal wedge angle $\beta_1$ and the distal wedge angle $\beta_2$ are the same ($\beta_1=\beta_2$) (symmetrical configuration) the reference plane of the wedge angle $\beta$ of the protective arrangement is identical to the plane of the protective arrangement maximum radius. A minimal difference between both planes, if therefore $\beta_1 \neq \beta_2$ has practically no significance so that they can be equated. It is therefore immaterial whether the reference plane is minimally proximally from the said protective arrangement maximum radius, that is to say $\beta_1<\beta_2$, or minimally distally from said protective arrangement maximum radius, that is to say $\beta_1>\beta_2$. All three above-mentioned variants are admissible and can be implemented in relation to different anatomical options of use.

In relation to a cervical spinal column however it is advantageous if $\beta_1>\beta_2$ because it is then markedly easier to penetrate into the tight interlaminar gap (between two vertebral arches) and the epidural space between bone and dura/spinal cord is tighter at the cervical spinal column than in the thoracic spinal column/lumbar spinal column.

In other words the geometry of the protective arrangement is different for the cervical spinal column. $\beta_1>>\beta_2$ should apply or the distal contact surface should be of a less convex configuration than in the case of a geometry intended for thoracic spinal column/lumbar spinal column, and should therefore be "flatter".

By pivoting or tilting the shaft out of the vertical it is now therefore possible to also operate inclinedly with the milling cutter.

The tilt angle $\kappa$ specifies the deflection of the axis of rotation of the shaft of the milling cutter from an ideally perpendicular vertical in the three planes (coronal, sagittal and transverse plane).

Two tilt angles in the sagittal plane define the tilt clearance available to the surgeon. On the one hand that is the optimum (recommended) tilt angle $\kappa_1$ which can be used in relation to ongoing use of the milling cutter and a greater, a maximum admissible but still safe tilt angle $\kappa_2$, which permits short-term use (<2.5 s) without a significant increase in the risk of injury.

The ranges of the two tilt angles $\kappa_1$ and $\kappa_2$ relate to the proximal wedge angle $\beta_1$ of the proximal wedge surface of the protective ring or the intermediate portion and the distal wedge angle $\beta_2$ of the distal wedge surface. It was found in development of the invention that that optimum tilt angle $\kappa_1$ is in the range $|\beta_2|<\kappa_1<-\beta_1$.

The maximum safe tilt angle $\kappa_2$ is in the range:

$$|\beta_2|<\kappa_2<-|\beta_2|, \text{ if } (90°-|\beta_2|)<\sigma$$

or $$|\beta_2|<\kappa_2<-\sigma, \text{ if } (90°-|\beta_2|)>\sigma.$$

In spite of that wedge-shaped configuration of the protective ring the protective ring does not have an acute angle with surfaces which converge pointedly towards each other at the radial outer edge, but is here rounded off at the radius "r" to avoid injuries and is therefore again of an atraumatic configuration. That basically wedge-shaped configuration of the protective ring is therefore also afforded when the proximal and distal sides of the protective ring are not in the form of straight surfaces but involve different geometrical shapes, for example being convexly or concavely curved, and therefore for example form a disc. This therefore involves a "basically wedge-shaped configuration" of the proximal and distal sides of the protective ring at least at the outer edge so that those sides or tangents thereto include an acute angle between them. The radius of that outer rounded configuration of the protective arrangement "r" should be in the following ranges in order to be able to easily get into the narrow interlaminar gap (between both vertebral arches) from the rear or under the bone edge (for example in the case of retrospondylophytes (posterior spondylophytes) at the cervical spinal column from the front) but without injuring the thin dura (that is typically of a varying thickness on average of 0.307±0.122 mm).

| Operating area | r |
|---|---|
| Cervical spinal column from ventral | 0.15-0.50 mm |
| Cervical spinal column from dorsal | 0.20-0.75 mm |
| Thoracic spinal column from dorsal | 0.33-0.75 mm |
| Lumbar spinal column from dorsal | 0.33-1.25 MM |

Embodiments of the invention provide that the protective arrangement vibrates and transmits same to the surrounding tissue, in which case the wedge-shaped configuration of the protective ring particularly advantageously contributes to gently loosening up the treated tissue.

Preferably a high impact frequency involving a low level of impact energy is thereby transmitted to the protective arrangement and thus the surrounding tissue is split into two layers (for example adhering dura, muscle or ligament attachments gently detached from the bone edge or periosteum).

The protective arrangement can have portions involving a number of geometries or different geometrical portions for implementing different functions. The provision of a first portion as a protective ring has proven to be particularly desirable, which surrounds the milling surface maximum radius or shields same at least distally and is of a markedly larger and preferably twice larger radial extent than a second portion distally adjoining the protective ring.

The protective arrangement can be fixed to the milling head in the form of a separate component. The fixer used can be for example a threaded pin, in particular with a hexagonal socket screw head. A protective collar therefore surrounds the fixer to prevent contact with the surrounding tissue so that the protective arrangement is therefore of a tissue-protecting nature for the fixer. The advantage of this configuration is that the surrounding tissue is treated carefully by the protective collar but at the same time the protective ring can be used for penetration into gap-shaped constrictions and to keep surrounding tissue away. The connector between the protective arrangement and the milling head however can also include a stem-mounted coupling ball which latchingly engages into an insert opening of corresponding configuration on the counterpart joint component and includes in particular an undercut configuration. This embodiment is appropriate in particular in a protective arrangement of plastic, in particular including PTFE/Teflon® which has the required flexibility for latching engagement into the counterpart joint component.

In a preferred development the configuration of the milling surface at the proximal side of the protective ring, preferably by means of a tooth arrangement or a diamond coating, also makes it possible to mill away at concealed locations which are of difficult access, for example boney structures (for example so-called osteophytes or spondylophytes), thereby permitting so-called "undercutting". That is a novel operating procedure which preferably makes it possible to remove distally deeper bone portions which are on the rear side in order to obtain the biomechanically relevant outer bone layer. That can now be milled away by virtue of the invention even without visual checking with high degree of safety.

The protective arrangement can be adapted to be releasably connectable as a protective attachment to the distal end of the milling head, this being effected for example by way of a latching connection, for example by way of a ball latch or by means of a screw connection.

The protective arrangement can be for example in the form of a protective cap which can be distally fitted on and which is of the geometry of a segment of a ball having a maximum radius greater than the milling surface maximum radius at the lower distal end of the milling cutter. Preferably that protective cap further includes a protective ring which peripherally encloses at least the lower end of the milling surface at the milling surface maximum radius, the protective ring projecting slightly beyond the milling surface maximum radial extent of the milling surface and therefore annularly enclosing that region.

The protective cap which is preferably in the form of a segment of a ball can possibly also include on its side which the upper side in the installation position a connecting ball which is shaped in one piece thereon and which can be latchingly inserted into a central recess of corresponding configuration on the inside of the milling cutter, into which that connecting ball can also be snappingly engaged. For that purpose the protective cap preferably comprises a thermally deformable material like for example Teflon® or another suitable biocompatible plastic which is known to the man skilled in the art. The connector between the milling surface or the milling head and the protective cap can also be adapted to permit a relative displacement between the components.

A further advantage of the protective arrangements being provided separately in the form of a protective attachment is that they can be stationary while the milling cutter fitted thereonto rotates so that the protective attachment functions as an attachment support which protects the tissue structures from injury due to the increased contact surface.

Certain embodiments have a non-rotatable connection between the protective arrangement and the milling cutter. Upon rotation of the milling cutter therefore the distal contact surface slides on the tissue. That attachment point or the attachment surface forms a kind of fixed point which slides distally on the tissue and permits substantially more precise milling because that stabilises the milling cutter and unwanted vibration is avoided (vibration damping). In addition that permits markedly improved handling (ergonomy) because the milling cutter no longer has to be held high and spaced from the tissue by the surgeon, but the milling cutter can be (slightly) supported at the distal edge of the bone and the tissue, even if only for a short time.

In other embodiments the protective arrangement is rotatably secured distally to the milling cutter, for which purpose preferably there is provided a bearing connection, for example in the form of a plain bearing, in particular including a ball joint. In that way the protective arrangement can be stationary in the milling operation and serves as a distal support bearing against the tissue. This can therefore provide a slightly elastic connection between the protective arrangement and the tissue. This configuration also provides that vibration is damped. It is important that, in the event of possible failure of the bearing connection, for example due to clogging or sticking, blood clots or the like the relatively moveable system then represents the non-rotatable embodiment without a risk of injury.

Vibration or oscillations of the milling cutter can adversely influence the milling process or even damage the surrounding tissue at points thereon. The enlarged distal contact surface functions as a support and a passive absorber for avoiding or reducing such vibration and thus stabilises the milling cutter. As possibly inevitable vibration is distributed to elastic tissue over the larger area of the protective arrangement injuries are reduced. At the same time however the elastic tissue also damps such vibration.

The protective arrangement can also include or consist of an elastic material (preferably PTFE/Teflon®, a biocompatible type of silicone or another elastic biocompatible material) in order to enhance that vibration-damping effect.

Excessive friction should not be exceeded in the operation because proteins suffer denaturation at temperatures above 42° C. Thermal insulation is implemented predominantly by the prevention of contact between the milling cutter which becomes hot and the tissue, in particular by virtue of the protective arrangement being of a configuration which is enlarged in a mushroom shape. In addition by virtue of the greater mass of the protective arrangement heat can be better dissipated so that cooling is markedly improved, which besides the purely geometrical configuration can also be effected by suitable materials. Continuous flushing of the working region for cooling purposes and for carrying away the bone meal from the grooves in the working part is however indispensible.

In a further embodiment the connector for connecting the protective attachment can be a protective tip which is provided at the distal end of the milling cutter and which narrows in the proximal direction from the diameter for forming an undercut configuration. For example a peripherally extending inner edge of a toroidal protective ring can be fitted into or snapped into that undercut configuration.

The connecting means between the protective attachment and the milling head however can also be designed to permit a relative movement between the parts.

Preferably the maximum periphery of the protective arrangement (protective arrangement maximum periphery) is about 1.5 to 2 times as great as the maximum periphery of the milling surface.

The invention thus permits an operating procedure using a milling cutter having a milling head which is provided on a shaft and which has a milling surface having a milling surface maximum radius and further includes a protective arrangement which peripherally surrounds at least the milling surface maximum radius and is of a protective arrangement maximum radius. In the operating procedure the milling cutter is introduced with the protective arrangement into a gap between two adjoining bones, for example vertebrae, so that the shaft of the milling cutter is driven by a drive unit and in that case tissue and/or the bone or bones is removed from a rear side with the proximal milling surface.

The operating procedure according to the invention permits for example a safe enlargement of the interlaminar gap and introduction of the milling head directly in the depth-wise direction (to the Lig. Flavum and dura) and milling from the inside outwardly or in terms of depth at the dura plane with an enlargement over all three bone layers of vertebral arches at the same time. That permits a higher level of milling efficiency with at the same time protection for the surrounding tissue by the protective arrangement.

In the operating procedure according to the invention the milling surface with the protective arrangement can be enclosed at the underneath edge of the bone whereby for the first time undercutting of the bone or hollowing out the bone below same from the inside is made possible to obviate biomechanically relevant instability. That novel operating process operates in that respect involving inclined insertion of the milling head into an opening from below or from the inside outwardly. In that case only the relevant constricting lower bone layers are removed, with the outer bone layers remaining untouched, so that for example the biomechanical function of a spinal column is maintained. Hitherto that has been only limitedly possible and involved more risks of injury.

In particular by virtue of the protective ring or girdle surrounding the milling surface at the maximum radius or periphery the milling cutter can be inserted in an angled condition into an opening between two bones. The milling cutter can then be driven and the inside tissue can be removed from the bone together with the bone itself by exerting a pulling force on the shaft, more specifically in any angular position and by applying any desired forces because the protective arrangement effectively protects the surrounding tissue structures from injury. That is of particular significance for example in the case of operations on the spinal canal because with existing operating procedures injuries easily occur. Substantially less experience and sensitivity is now required from the operator. For example the milling cutter can be introduced into the interlaminar window of two vertebral arches between two vertebral joints. As substantially higher forces can be applied and the risk of unwanted injury is completely eliminated it was possible with the procedure according to the invention for the operating time on a spine to be reduced from 25 minutes to 5 minutes.

As a result the new operating procedure can be carried out more quickly, substantially more efficiently and more safely with at the same time a reduction in intraoperative complications. This affords considerable medical, social and economic advantages.

The invention thus also makes it possible to provide for robot-assisted inventions, for example at the spinal column, in which case a rotating milling head is inserted in an automatic procedure to the location of application without visual checking, that is to say so-to-speak "blind", and bone is milled away in the return movement or by movement to the side.

The milling cutter according to the invention can even be used in an automated or robot-assisted procedure so-to-speak "blind" because many inaccuracies and errors can be eliminated in the steps of introducing, using and guiding the milling cutter.

The operating procedure according to the invention thus both reduces the in-patient stay, reduces the number and frequency of complications and revision operations and possible readmissions and reduces post-operative incapacity for work.

In particular the proposed operating procedure is advantageous in relation to endoscopic interventions because that area basically involves having to work in a 2-dimensional "flat" field (without sharpness of depth) and all deeper structures optically merge with the foreground. Probable localization of the structures which are not always visible is thus implemented on the basis of anatomical preliminary knowledge, imaging diagnostics and in particular the experience of the operator.

The novel procedure can be used both in the initial phase of any intervention at the spinal column (cervical, thoracic and lumbar spinal column) by way of a dorsal access (from behind, from the rear side) and also in a further phase of an operation ventrally (from the front) at least without any doubt at the cervical spinal column.

Dorsally the vertebral arches (lamina) of two are disposed in portion-wise overlapping adjoining relationship, similarly to roof tiles, with a narrow gap therebetween in superposed relationship.

A blunt object can be introduced into that narrow space of less than 3 mm without an increased risk of injury because action is implemented between two bone layers. Hitherto dorsal access to the spinal canal has been effected by means of the "enlarged interlaminar window". In the case of that known operating procedure the bone substance is removed layer-wise with a milling cutter as far as the dura in order to obtain a "window" for the access and then to be able to continue with the actual intervention (for example removal of a herniated disc or a tumour) under visual checking. Enlarged accesses are referred to as hemilaminectomy (removal of a half of the vertebral arch) or laminectomy (on both sides). What is important is that that gap ends in the direction of the spinal canal at the yellow ligament (lig. flavum) or without transition directly at the dura, which increases the injury risk extremely.

In the preferred operating procedure firstly the upper (surface) lamina is milled away with an advance direction towards the head and then the lower (deeper) lamina is removed with a feed direction towards the feet, in which case the protective arrangement is disposed on or at the dura.

The wedge-shaped configuration according to the invention of the protective ring on the milling cutter means that it is now possible for the first time to go gently into that narrow gap with and without rotation of the milling cutter, that is to say in the switched-off condition. By virtue of the lever arm formed by the protective ring it is possible to enlarge the bone gap between the vertebrae slightly by about 0.5-2 mm with the protective ring. That is further facilitated by the wedge-shaped configuration. The fulcrum as the pivot point of the lever is on the contact surface of the opposite protective arrangement distal surface and the upper surface of the deeper vertebral arch. In that way the surgeon can work in the depth direction layer-wise with the milling cutter.

With a non-rotatably fixed wedge-shaped protective arrangement slight vibration or oscillation is even highly advantageous because it is possible to use that slight vibration of the milling cutter by rhythmically introducing the wedge shape for enlargement of the gap. In that way for example adhesions (adhesions of the connective tissue and adhesion of the dura), attachments of the ligaments and so forth are gently and safely released or obtusely broken up.

With the operating procedure according to the invention three penetration mechanisms can be used alternately or simultaneously by the milling cutter, namely the lever arm formed by the protective ring or the protective arrangement, the wedge shape and vibration.

Possible areas of use of the milling cutter and the operating procedures carried out therewith are set forth by way of example and without limitation in the Table below:

| Access/discipline | Intervention or direct location of use of new milling heads | Examples of the underlying pathologies and diseases |
| --- | --- | --- |
| Dorsal access to the lumbar and thoracic spinal column—open microsurgery and endoscopically | Laminectomy, hemilaminectomy, partial-hemilaminectomy, enlarged interlaminar window, bone decompression of spinal and root canal (spinal canal), spinal fusion (PLIF, TLIF etc), laminoplasty | Spinal canal stenosis (constriction of spinal canal), vertebral disc herniation LSC, spondylolisthesis, trauma consequences, for example fractures, instabilities, bleeds, tumours, for example ependymoma, meningeoma, neurinoma, inflammation (abscess, spondylodiscitis) |
| Ventral access to the LWC and TWC open and thoracoscopically | Osteophytes removal, bone decompression, stabilisation, vertebra replacement implantation, fusion (ALIF), vertebral disc prostheses implantation | Spinal canal stenosis, vertebral disc herniation, spondylolisthesis, trauma consequences, for example fractures, instabilities, bleeds, tumours, for example ependymoma, meningeoma, neurinoma, inflammation (abscess, spondylodiscitis) |
| Dorsal access to the cervical spinal column | Frykholm's operation, laminectomy, hemilaminectomy, laminoplasty, bone decompression of the spinal canal | Spinal canal stenosis, vertebral disc herniation, spondylolisthesis, trauma consequences, for example fractures, facet joint (sub) luxation, instabilities, bleeds, tumours, for example ependymoma, meningeoma, neurinoma, inflammation (abscess, spondylodiscitis) |
| Ventral access to the LSC | Microdiscectomy and fusion (ACDF), uncoforaminotomy, ventral bone decompression, osteophyte removal | Spinal canal stenosis, vertebral disc herniation, bleeds, tumours, for example ependymoma, meningeoma, neurinoma, inflammation (abscess, spondylodiscitis) |
| Transnasal-transsphenoidal access microsurgically and endoscopically | Enlargement of the window from the sphenoid sinus, access to the sella turcica | Pituitary processes, for example adenomas |
| Retrosigmoidal and subtemporal access | Partial petrosectomy, enlargement of the inner ear canal | Acoustic neuroma, meningeoma |
| Base of the skull surgery, various accesses | Preparation of various nerves and vessels at the base of the skull, in the foramen magnum, petroclivally, foramen jugulare, cavum meckeli | Various processes |
| Oral and maxillofacial surgery | Sinus lift | Preparation measure for dental implants |
| Oral and maxillofacial surgery | Preparation and transposition of nervus alveolaris inferior in the canalis mandibulae ab foramen mentale | Preparation measure for dental implants |
| Endoscopic jaw and frontal sinal cavity surgery | Various mucous membrane and vessel-treating interventions | Insertion tube operation |
| Minimally invasive foot surgery | Cutting/shortening bones by way of point incision | For example halux valgus operations |
| Arthroscopy of various joints | Osteophyte removal | |

The protective arrangement can thus involve for example different convexities as required adapted to the prevailing anatomical conditions and thus determine the space or the so-called safety spacing relative to the soft tissue parts.

In accordance with the invention many other configurations of the protective arrangement of the milling cutter, for example the protective girdle and protective cap thereof, are possible, thus for example:
    different geometrical configurations of the milling head, thus for example also variable convex, straight or concave sub-shapes,
    various configurations for the tooth arrangement or diamond coating for the sharp milling surface,
    the extent of extension of the sharp milling surface to the proximal, radial edge of the protective ring,
    different geometrical shapes in terms of size, thickness, length or periphery and also the degree of angle of the convexity—independently concerning the protective girdle or protective ring and also the smooth protective cap.

The geometrical configuration of the milling head determines the possible safe tilt angle in the milling operation. Therefore depending on the anatomical conditions and the desired end result the operator selects a suitable milling cutter which is appropriate for the situation of use, with its protective arrangement.

The distal protective arrangement which preferably goes into a concentric projecting protective collar is preferably of such a configuration that it can slide without friction over all structures disposed therebeneath and therebeside and at the same time can keep those delicate structures gently away from the sharp cutting edges/sharp friction surface of the working part.

In the specific description hereinafter reference is made to the accompanying drawings which form part of this description of the invention and which show specific embodiments with which the invention can be carried into effect for illustration purposes. In that respect directional terminology like for example "up", "down", "front", "rear", "forward", "rearward" and so forth are used in relation to the orientation of the respectively described Figure. As components of embodiments can be positioned in a number of different orientations the directional terminology serves for illustration purposes and is in no way limiting. It will be appreciated that other embodiments can be used and structural or logical modifications can be effected without departing from the scope of protection of this invention. The specific description hereinafter is not to be interpreted limitingly.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the context of this description the terms "connected", "attached" and "integrated" are used to describe both a direct and also an indirect connection, a direct or indirect attachment and direct or indirect integration. In the Figures identical or similar components are denoted by identical references insofar as that is appropriate.

Figure 9:
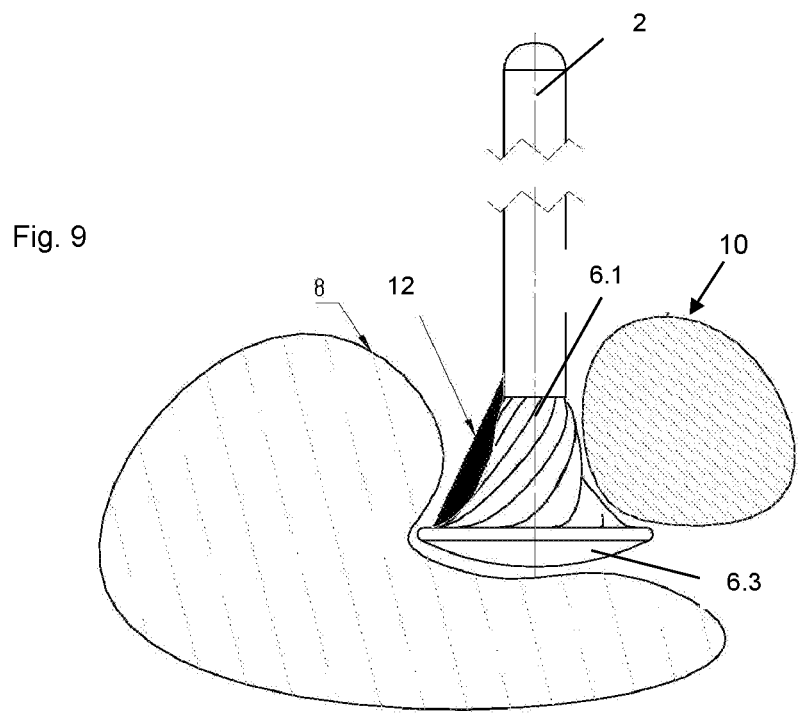

Reference lines are lines connecting the reference numeral to the part in question. In contrast an arrow which does not touch any part relates to the entire unit towards which it is directed. The Figures moreover are not necessarily true to scale. To illustrate details certain regions are possibly shown on an enlarged scale. In addition the drawings can be strikingly simplified and do not include every detail which is possibly present in a practical configuration. The terms "up" and "down" relate to the illustration in the Figures.

Figures 37, 38:
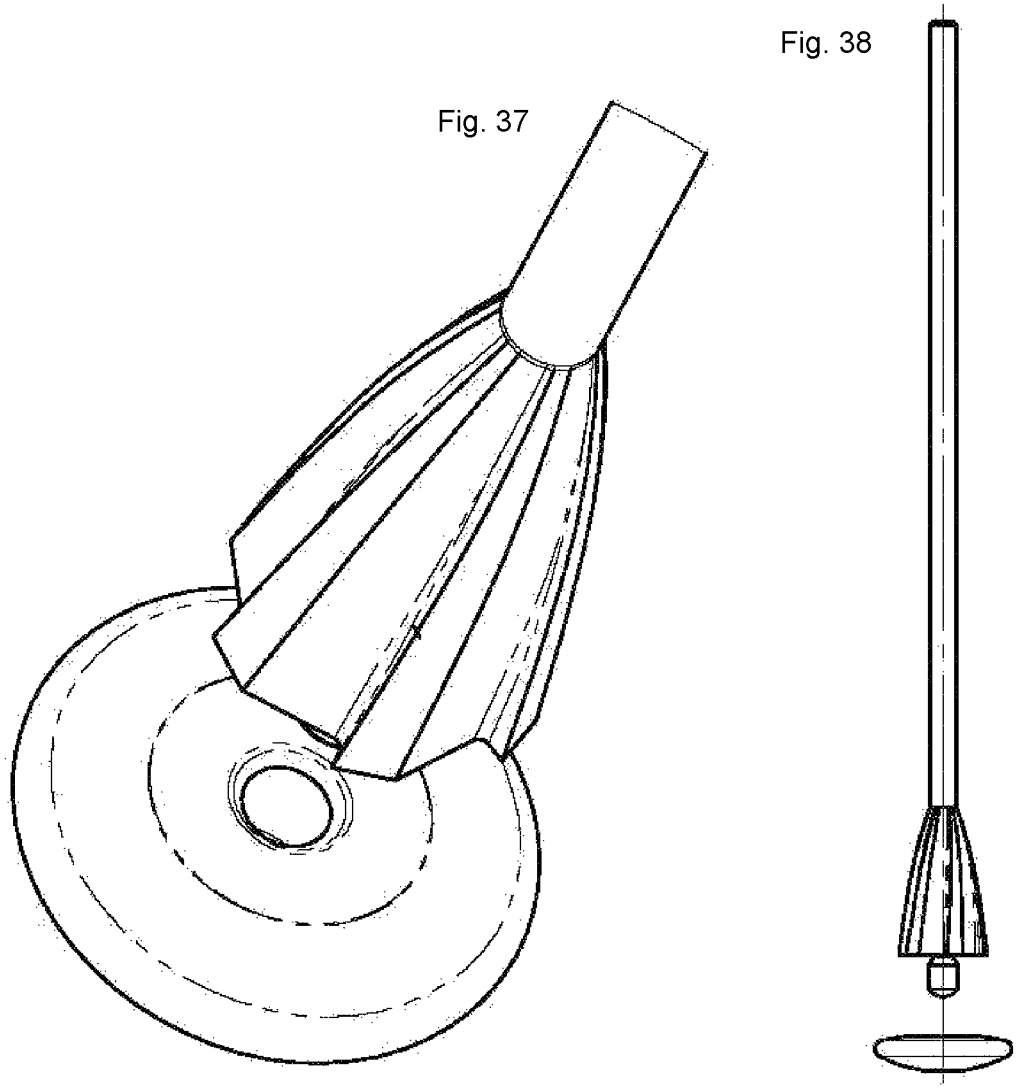
Figure 39:
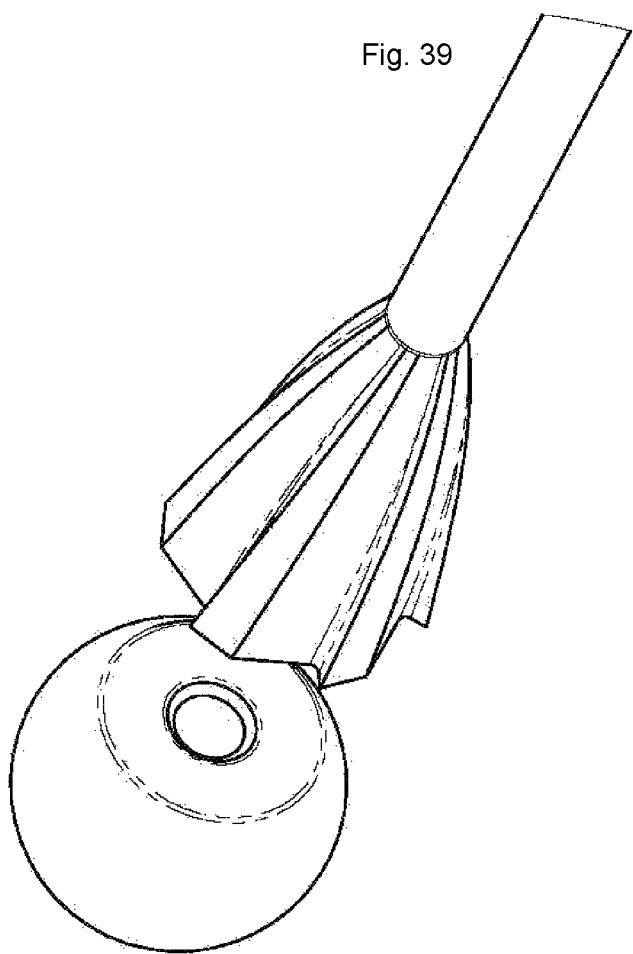
Figure 40:
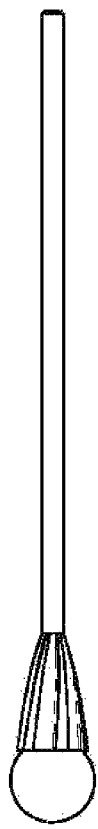
Figure 42:
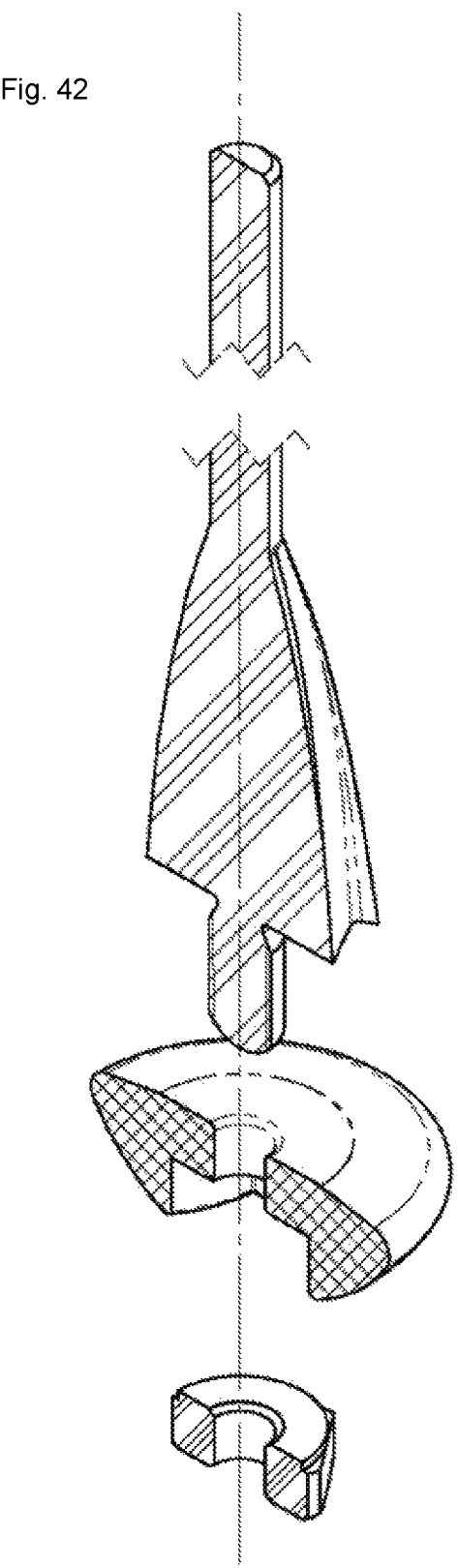
Figure 44:
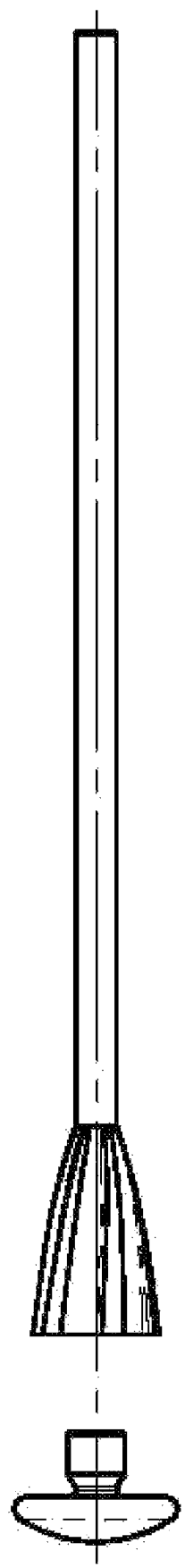
Figure 45:
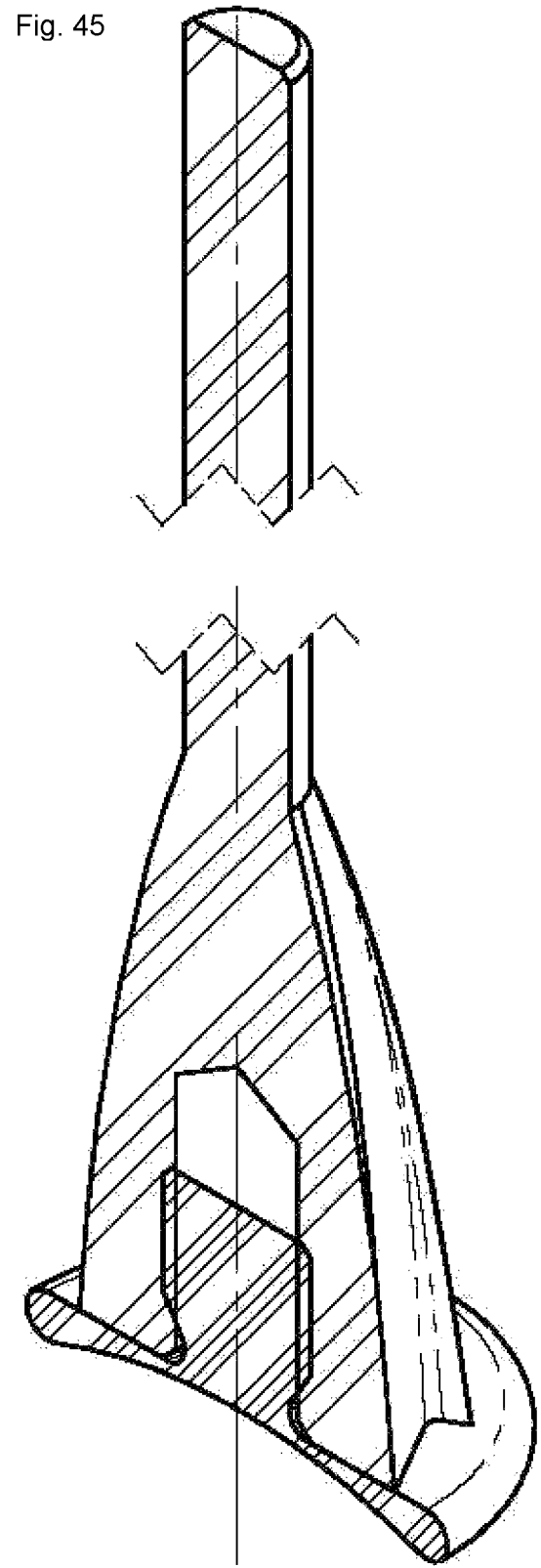
Figure 46:
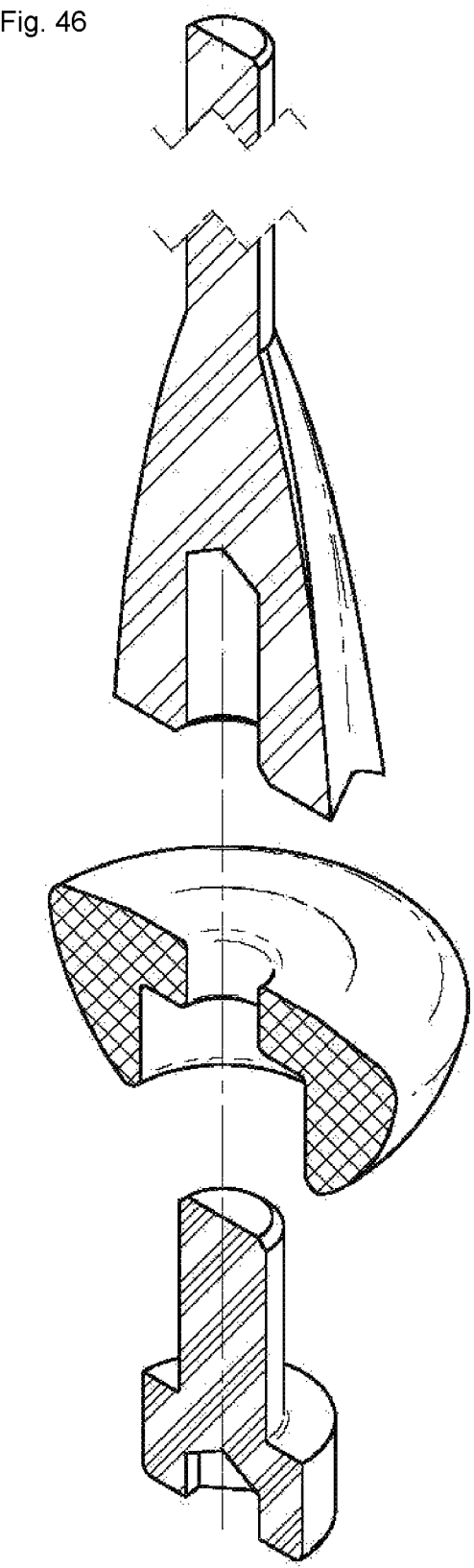
Figure 47:
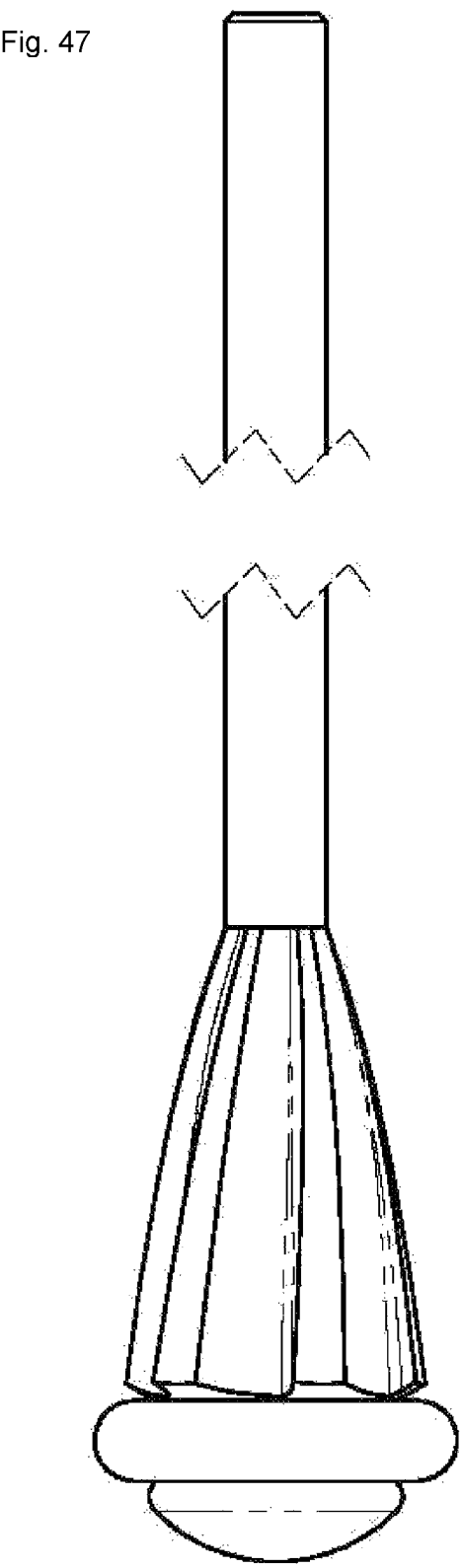
Figure 48:
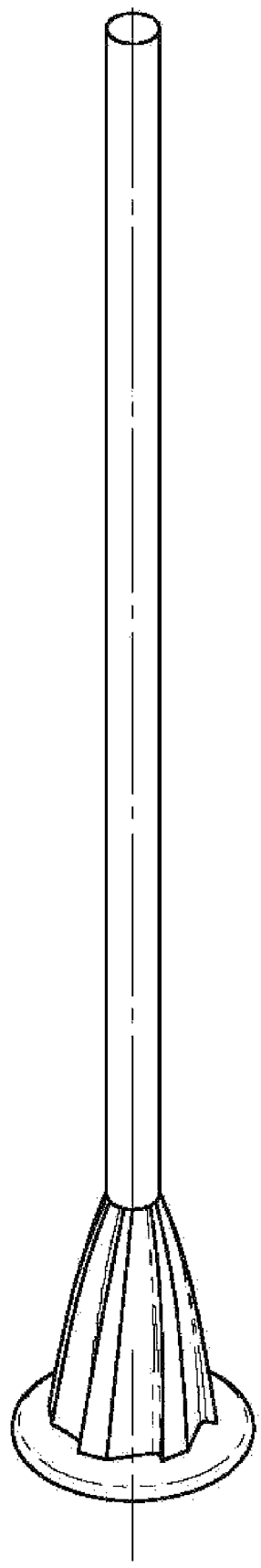
Figure 49:
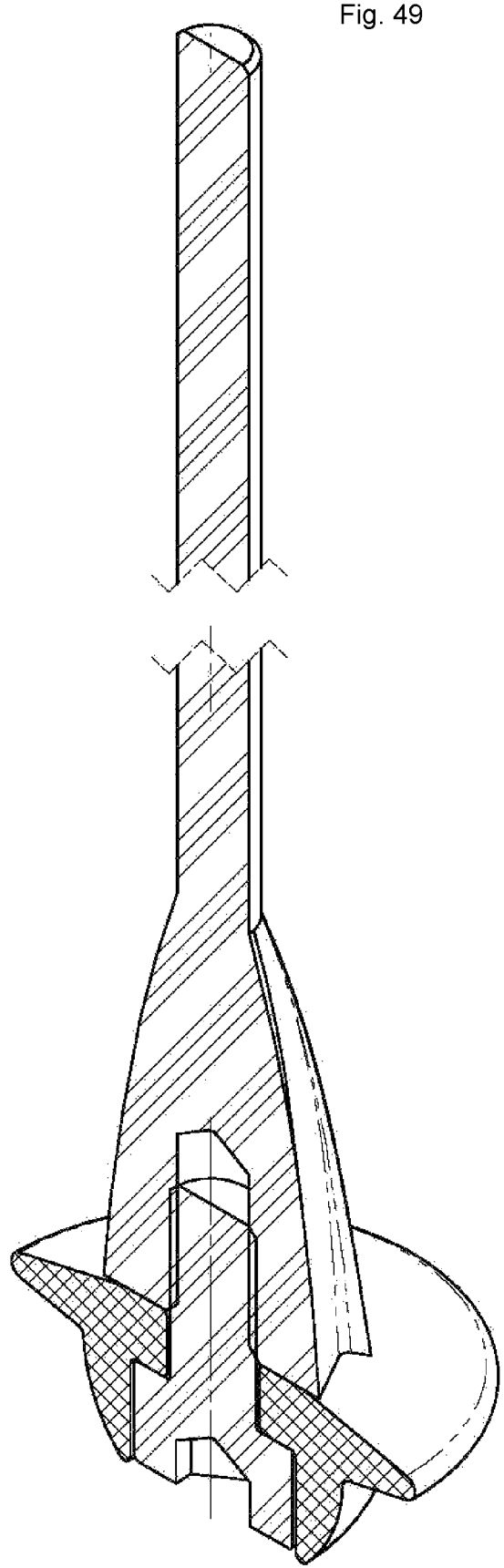
Figure 50:
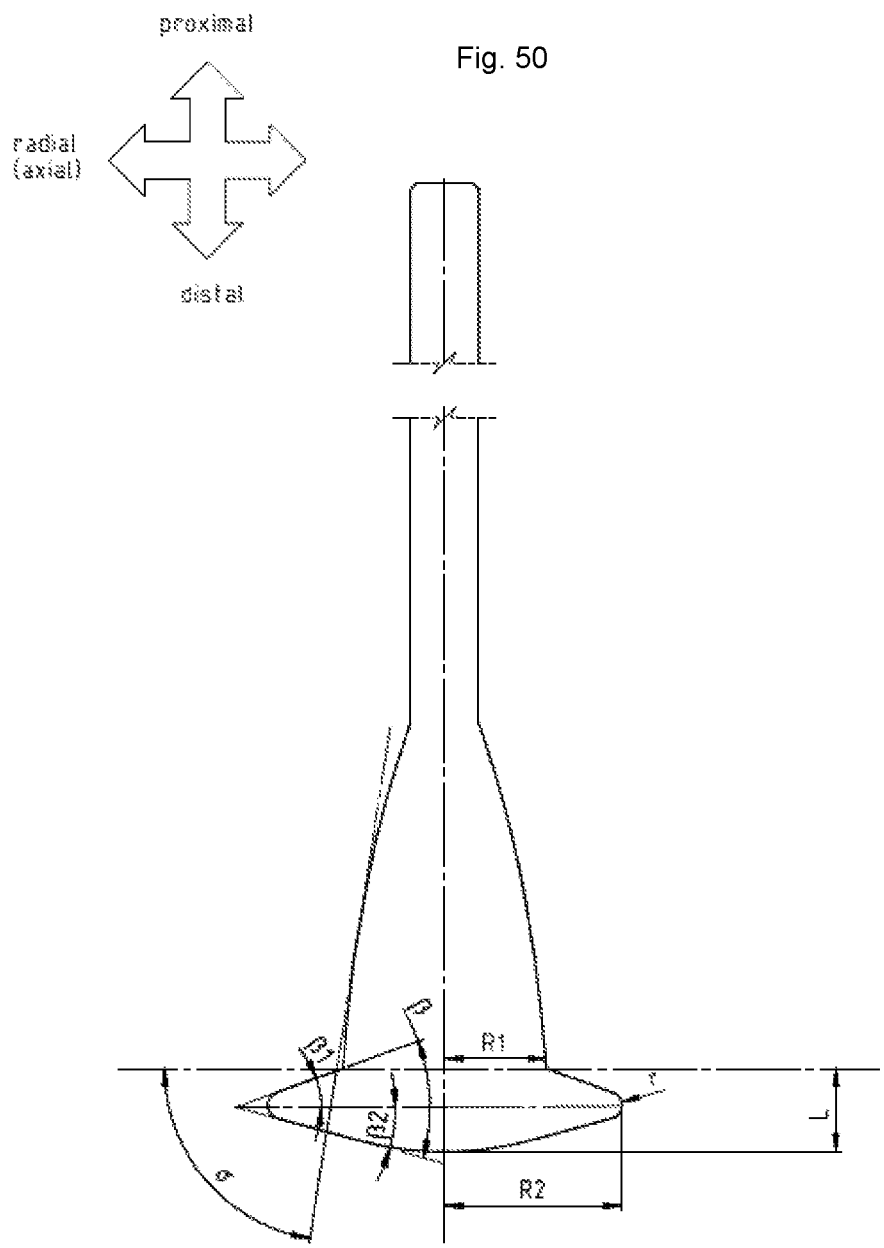

In the drawings:

FIG. 1 shows a side view of a first embodiment of a milling cutter according to the invention;

FIG. 2 shows a plan view of the milling cutter of FIG. 1;

FIG. 3 shows a cross-section of the milling cutter of FIG. 1;

FIG. 4 shows an enlarged perspective view of the milling head of the milling cutter of FIG. 1;

FIG. 5 shows a side view of a second embodiment of a milling cutter according to the invention;

FIG. 6 shows a plan view of the milling cutter of FIG. 5;

FIG. 7 shows a cross-section along line B-B in FIG. 6;

FIG. 8 shows an enlarged perspective view of the milling head of the second embodiment;

FIG. 9 shows the protective zone formed by the configuration according to the invention of the milling head, the protective zone surrounding the adjacent vulnerable tissue in the milling operation;

FIG. 10 shows an enlarged isometric plan view of the milling head of a third embodiment with the protective cap removed, FIG. 11 shows an isometric side view of the third embodiment from below;

FIG. 12 shows an isometric side view of the third embodiment;

FIG. 13 shows a shortened side view of the third embodiment;

FIG. 14 shows an enlarged cross-section of the milling head of the third embodiment;

FIG. 15 shows an enlarged isometric plan view of the milling head of a fourth embodiment with the protective ring removed;

FIG. 16 shows a perspective view of the fourth embodiment from below;

FIG. 17 shows an enlarged cross-section of the milling head of the fourth embodiment with the fitted protective ring;

FIG. 18 shows a side view of the fourth embodiment;

FIG. 19 shows an enlarged isometric plan view of a fifth embodiment with the protective cap removed;

FIG. 20 shows an enlarged isometric view of the fifth embodiment with the protective cap removed from below;

FIG. 21 shows an enlarged lateral sectional view of the fifth embodiment with the protective cap fitted;

FIG. 22 shows a shortened side view of the fifth embodiment;

FIG. 23 shows an isometric side view of the fifth embodiment;

FIG. 24 shows a side view of a sixth embodiment with a spherical milling head and a protective girdle;

FIG. 25 shows a side view of a seventh embodiment of a milling head with flattened protective cap and protective girdle;

FIG. 26 shows an enlarged isometric side view of a milling head of an eighth embodiment with the protective cap removed;

FIG. 27 shows an enlarged isometric view of the milling head of the eighth embodiment from below;

FIG. 28 shows another enlarged isometric plan view of the eighth embodiment with the protective cap fitted;

FIG. 29 shows an enlarged cross-section of the milling head of the eighth embodiment in centered orientation of the protective cap in relation to the milling head;

FIG. 30 shows a reduced-scale cross-section of the milling head of the eighth embodiment with the protective cap in displaced orientation in relation to the milling head;

FIG. 31 shows a side view of the eighth embodiment;

FIG. 32 shows an enlarged side view of a milling head of a ninth embodiment with a flat top side on the protective ring;

FIG. 33 shows an enlarged side view of a milling head of a tenth embodiment with a disc-shaped protective ring with identical curvature on the top side and the underside;

FIG. 34 shows an enlarged side view of a milling head of an eleventh embodiment with a protective ring with an only slightly curved underside and a more greatly curved top side;

FIG. 35 shows an isometric view from below of a twelfth embodiment with a threaded pin at the distal end of the milling surface, which can be turned into a threaded opening arranged centrally in a protective ring;

FIG. 36 is an isometric cross-section of the eleventh embodiment of FIG. 35;

FIG. 37 is an isometric plan view of a thirteenth embodiment with a threaded pin which projects distally from the milling surface and on to which a protective arrangement in the form of a protective cap can be screwed;

FIG. 38 shows a side view of the thirteenth embodiment of FIG. 37 with the protective cap removed;

FIG. 39 shows an isometric plan view of a fourteenth embodiment with a protective arrangement in the form of a protective ball with a contact surface which is flattened at the top side, which can be screwed on to the threaded pin of the milling cutter, that projects distally from the milling surface;

FIG. 40 shows a side view of the fourteenth embodiment of FIG. 39;

FIG. 41 shows an isometric longitudinal section of a fifteenth embodiment with a protective cap which is closed at the front side and which can be screwed with a central threaded hole on to the threaded pin projecting distally from the milling surface;

FIG. 42 shows an isometric longitudinal section of a sixteenth embodiment with a protective arrangement in the form of a protective ring, which preferably comprises ceramic and can be fixed by way of a nut to the threaded pin projecting distally from the milling surface, wherein provided for receiving same at the distal lower end is a nut receiver functioning as a seat for the nut;

FIG. 43 shows an isometric longitudinal section of a seventeenth embodiment with a disc-shaped protective arrangement having a threaded pin on the proximal top side, which can be screwed into a threaded hole at the distal end of the milling cutter;

FIG. 44 shows a side view of an eighteenth embodiment with a protective arrangement screwed into the threaded hole on the milling head, with a slightly convexly curved distal contact surface;

FIG. 45 shows an isometric longitudinal section of a nineteenth embodiment with a disc-shaped protective arrangement and a concavely curved distal protective surface, which can be screwed by means of a proximal threaded pin into the threaded hole at the distal end of the milling cutter;

FIG. 46 shows an isometric longitudinal section of a twentieth embodiment with a protective arrangement in the form of a protective ring, which can be screwed fast to the distal end of the milling head by means of a threaded pin which in the installation position is accommodated in a distal mounting opening in the protective ring;

FIG. 47 shows an enlarged side view of a twenty-first embodiment with a protective ring projecting distally from the milling surface maximum radius and projecting radially beyond same and which is snap-engaged on a corresponding seat at the distal end of the milling cutter;

FIG. 48 shows an isometric plan view of a twenty-second embodiment with a protective ring which is snap-engaged on to the distal end of the milling cutter distally from the milling surface maximum radius by engagement on to a seat;

FIG. 49 shows an isometric longitudinal section of a twenty-third embodiment with a protective attachment which is fixed distally to the milling surface by way of a fixing bolt with a hexagonal socket and which has a first disc-shaped portion adjoining the milling surface maximum radius of the milling surface, which forms a protective ring around the milling surface maximum radius with doubling of the outside radius thereof and which is adjoined extending distally by a protective collar of an arcuate configuration at the outward side for centrally receiving the fixing bolt, which is of a radial extent of approximately the milling surface maximum radius;

FIG. 50 shows a longitudinal section of a milling cutter according to the invention to illustrate the terms and angles used; and FIGS. 51 to 55 show side views of the use of a milling cutter according to the invention in an operating procedure according to the invention at two cervical vertebral arches (lamina), for example a Frykholm's operation, interlaminar windowing and hemilaminectomy.

DETAILED DESCRIPTION OF THE INVENTION

All embodiments are of a rotationally symmetrical configuration relative to the center line of the milling cutter.

The milling cutter shown in FIG. 1 accordingly primarily comprises the shaft 2 having a top proximal end for non-rotatable connection to a known drive device and a complex milling head 4 at the front distal end which is of a complex geometry.

The milling head 4 includes a proximally oriented or operative sharp milling surface 4.1 (here with a tooth arrangement) which from the outer peripheral surface of the shaft 2 enlarges in the distal direction to a maximum periphery where there is a protective ring 4.2 surrounding the maximum periphery in an annular configuration and projecting markedly radially outwardly beyond the maximum periphery. Provided at the distal front end of a somewhat reduced radius is a distal convex protective cap 4.3 which is set back or recessed in relation to the protective ring 4.2.

As can be clearly seen the milling surface 4.1 extends only to the maximum periphery and then goes into the rounded protective ring 4.2 which surrounds that maximum periphery in an annular configuration in the form of a radial ring. In an operation that protective ring 4.2 can be pushed without causing injury into the tissue, more specifically even when the milling cutter is rotating, because the protective ring 4.2 like all other surfaces apart from the milling surface is edge-free and of a rounded configuration.

Like the first embodiment shown in FIGS. 1 to 4 the second embodiment shown in FIGS. 5 to 8 of the milling cutter is also provided with a milling head 6 of an alternative configuration, but this milling cutter is also in the form of a one-piece turned part. In this second embodiment the protective cap 6.3 however is of a convex mushroom-shaped configuration, in contrast to the first embodiment this is larger and extends continuously without a recess from the outer edge of the protective ring 6.2, whereby the protective cap 6.3 and the protective ring 6.2 therefore form a continuous segment of a ball with a larger distal contact surface than the first embodiment.

FIG. 9 shows an enlarged side view of a milling cutter introduced in an operation between diagrammatically indicated tissue 8 and bone structures 10 for illustrating the three-dimensional protective zone 12 formed by the protective ring 6.2 of the protective arrangement. That three-dimensional protective zone 12 is shown in black and is defined radially at the outside by the connecting line from the outside edge of the protective ring 6.2 or the protective cap 6.3 to the proximal end of the milling surface 6.1 and at the inside by the milling surface 6.1 itself. The rotational body of that region forms the three-dimensional protective zone 12 around the milling surface 6.1, in relation to the surrounding tissue or the bone 10, into which no tissue 8 passes. In other words: the protective arrangement is such that the protective zone 12 is always free from tissue 8 during the operation. The further the protective ring 6.2 or the protective cap 6.3 projects beyond the milling surface 6.1 or the larger the maximum diameter thereof is, the correspondingly further is the maximum periphery of the milling surface 6.1 enlarged and correspondingly larger is the protective zone formed around the milling surface 6.1.

It is possible to clearly see how the protective cap 6.3 can be applied to the tissue and thus with enlargement when applying pressure the surface pressure applied to the tissue is reduced in that way but at the same time the milling cutter can be used with its milling surface 6.1 operating exclusively in a proximal relationship in order to proximally removed the adjoining bone 10.

The protective function produced by the geometrical configuration is clearly apparent in FIG. 9. In order carefully to push aside or separate the tactile soft tissue pieces from the bone pieces 10 to be milled away and at the same time to ensure good bonding to the bone the geometry of the milling head can be mushroom-shaped in accordance with the second embodiment, in which case the distal surface of the protective cap 6.3 and the protective ring 6.2 is polished smooth or is coated in such a way that, by virtue of the protective ring 6.2, all edges are rounded off and the sharp working surface ends in proximal relationship with the lateral edge of the protective ring 6.2 before the region of the maximum radial extent.

FIGS. 10 to 14 show various views of a third embodiment of a milling cutter in which the milling head 14 is again provided in one piece at the lower end of the shaft 2 and, forming the milling surface 14.1, extends in a continuously enlarging configuration from the outer peripheral surface of the shaft 2 to a lower maximum periphery, and there goes into an upper circular plate 14.2, wherein distally spaced therefrom by way of a reduced undercut portion there is provided a lower circular plate 14.2 so that there is a peripherally extending groove between the circular plates 14.2 and 14.3. The protective cap 16 which comprises plastic with a PTFE/Teflon® coating and which is of a toroidal configuration can be inserted into that groove, the protective cap being convexly curved on the proximal and distal sides, like a flying saucer. The outside radius of the protective cap 16 is approximately twice as great as the maximum radius of the milling surface 14.1 at the distal end. On the top side the protective cap 16 has an insertion opening 16.1 of corresponding configuration, with a peripherally extending, inwardly projecting elastic edge 16.2 so that the lower circular plate 14.5 can be fitted into the insertion opening 16.1 and the edge 16.2 in the installed position engages into the peripheral groove in the milling head 14 and thus connects the protective cap 16 releasably but captively to the milling head 14, wherein in this embodiment the distal end of the protective cap 16 forms the contact surface.

In the fifth embodiment shown in FIGS. 16 to 18 the milling surface 18.1 of the milling head 18 is as in the fourth embodiment, but the fixing end which is provided distally from the milling surface 18.1 is of a somewhat different configuration, more specifically with a more greatly convexly curved distal contact surface 18.3 and an undercut configuration which proximally adjoins same and which is reduced in size in relation thereto, to form the seat for the protective ring 20 which can be snap-engaged into place, which in this fifth embodiment therefore forms the protective arrangement, in conjunction with the distal contact surface 18.3. That protective ring 20 is in turn in the form of a toroidally closed ring body having a central insertion opening 20.1, the inside diameter of which is smaller than the maximum diameter of the distal contact surface 18.3 which is formed on the milling cutter in one piece distally beneath the milling surface 18.1. That configuration means that the elastic protective ring 20 can be snap-engaged captively but releasably on to the seat of the milling head 18, formed by the undercut configuration. In this embodiment the contact surface 18.3 with the protective ring 20 fitted thereon forms the distal contact surface of the protective arrangement.

FIGS. 19 to 23 show various views of the sixth embodiment with a protective arrangement in the form of a protective cap 22 in which the distal contact surface is in the form of a spherical cap 22.3. At the proximal end the protective cap 22 has a stem-mounted coupling ball 22.4 which is formed in one piece and which can be inserted releasably and captively in latching engagement into an insertion opening 24.5 of corresponding configuration at the distal front end of the milling head 24. At the distal end of the milling surface 24.1 the milling head 24 has a circular plate 24.4 forming the milling surface maximum radius of the milling surface 24.1. In the installation position that circular plate 24.4 engages into an annular seat 22.5 of corresponding configuration on the proximal end of the protective cap 22. Provided on the protective cap 22 radially outwardly and annularly surrounding the seat 22.5 is a protective ring 22.6 which projects in the proximal direction beyond the circular plate 24.4 and thus embraces same at the outside in the installation position.

FIGS. 24 and 25 show the seventh and eighth embodiments of the atraumatic milling cutter, the milling surfaces 26.1; 28.1 of which are each spherical.

In the seventh embodiment shown in FIG. 24 the milling surface 26.1 and the protective cap 26.3 are both spherical, wherein the proximal milling surface 26.1 is coated with diamonds and the distal protective cap 26.3 extends proximally upwardly beyond the maximum radius to form a peripherally surrounding protective girdle 26.4.

The eighth embodiment shown in FIG. 25 also provides that the milling head 28 is spherical at least on the proximal milling surface 28.1 and is coated with diamonds. The distal contact surface 28.3 is however flattened in relation to the seventh embodiment, and therefore involves a markedly larger radius than the proximal milling surface 28.1 of the milling head 28, but is also in the form of a smooth protective cap 28.3 which peripherally completely embraces the distal end and extends proximally beyond the maximum radius of the milling head 28 once again to form a protective girdle 28.4.

The ninth embodiment shown in FIGS. 26 to 31 primarily differs from the fifth embodiment shown in FIGS. 20 to 23 in terms of the connecting means between the protective arrangement in the form of the protective cap 32 and the milling head 30. Provided at the distal end of the milling head 30 distally from the maximum radius 30.2 of the milling surface 30.1 is an insertion opening 30.3 into which a stem-mounted coupling ball 32.4 can be releasably inserted, therefore being a coupling ball 32.4 formed in one piece by way of a stem on the proximal surface of the protective cap 32. A certain oversize of the insertion opening 30.3 with respect to the outside diameter of the coupling ball 32.4 allows a relative displacement between the protective cap 32 and the milling head 30, preferably in the region of 0.5 to 1 mm. That relative displacement permits a possible deviation in the coaxial relationship of the protective arrangement from the axis of rotation of the milling cutter and thus provides improved adaptability, in particular in tight anatomical conditions.

FIGS. 32 to 34 then show various embodiments of milling heads 34, 36, 38 with protective rings 34.2; 36.2; 38.2 which are of different configurations and which are formed thereon in one piece, and with distal contact surfaces 34.3; 36.3; 38.3, which project radially beyond the respective milling surface maximum radius of the distal ends of the milling surfaces 34.1; 36.1; 38.1. The differences here substantially concern the geometrical configuration of the protective arrangements, in particular the proximal top sides of the protective rings 34.2; 36.2; 38.2 which surround the milling surfaces 34.1; 36.1; 38.1 in a plate shape.

The embodiments of FIGS. 35 to 47 represent various embodiments in which the connector between the milling head and the protective arrangement are in the form of a screw connection.

The embodiments of FIGS. 35 to 42 are in the form of male screw connections, in which provided at the distal end of the milling head, being the lower end in the Figures, is a threaded pin projecting along the central axis of rotation and on to which either the protective arrangement can be directly screwed with a female thread of complementary configuration, or, in accordance with the FIG. 42 embodiment, provided at the distal lower end of the annular protective ring is a nut receiving means, therefore being a receiving opening which is complementary to the nut and in which the nut non-rotatably fits and at the same time is shielded by the surrounding protective arrangement from the surrounding tissue to prevent unintended injury.

In contrast the embodiments shown in FIGS. 43 to 46 show the female configuration of the screw connections, in which a respective threaded peg or threaded pin is provided on the protective arrangements at the top sides which are proximal in the installation position, which peg or pin can be screwed into a threaded opening of complementary configuration at the inside of the distal lower end of the milling head. The embodiment of FIG. 46 is especial in that respect because therein the connection is made by way of a separate nut which is fitted enclosed in a distal pin receiving means in the protective arrangement.

FIGS. 51 to 55 show various views to illustrate the operating procedure according to the invention using a milling cutter 40 according to the invention. The milling cutter 40 includes a milling surface 40.1 which enlarges conically continuously from the milling surface proximal end to the milling surface distal end, with spiraled cutting edges, as well as a disc-shaped protective arrangement 40.2 which approximately doubles the milling surface maximum radius at the milling surface distal end.

Figure 51:
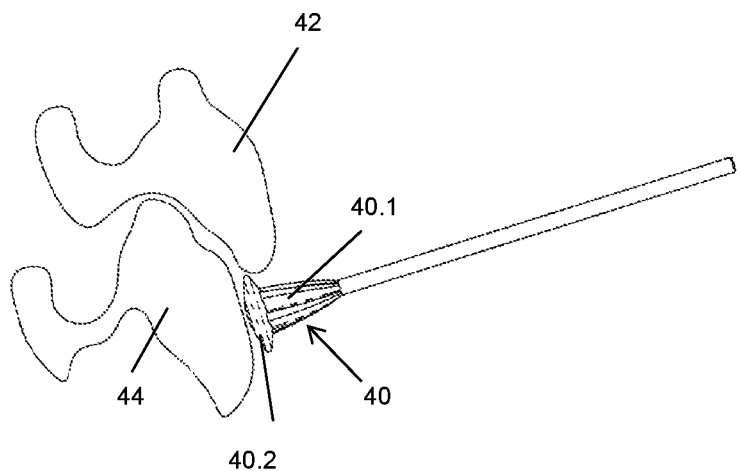

In FIG. 51 the milling cutter is arranged before the beginning of the intervention between an upper lamina 42 and a lower lamina 44 adjoining same. Firstly the surgeon pushes the milling cutter 40 laterally into the interlaminar gap between the upper lamina 42 and the lower lamina 44.

Figure 52:
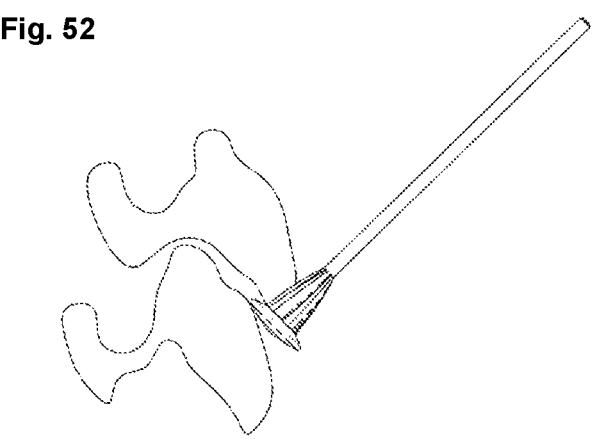

Then as shown in FIG. 52 the lower end of the upper lamina 42 is milled away, in which case the protective arrangement 40.2 penetrates into the interlaminar gap, with the proximal support surface and the distal contact surface of the protective arrangement 40.2 being guided at the upper lamina 42 and the lower lamina 44.

Figure 53:
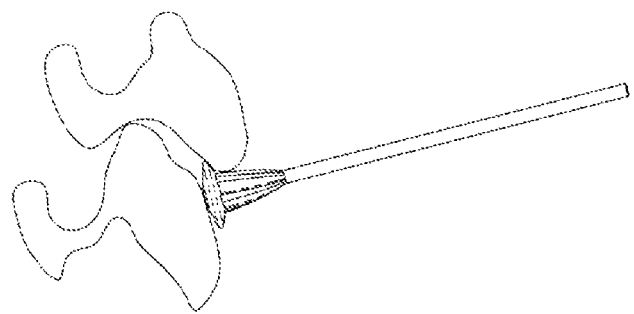
Figure 54:
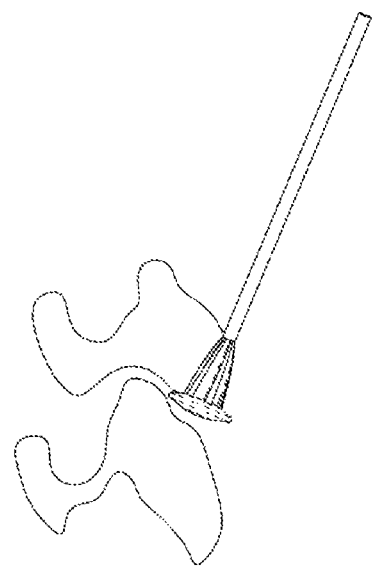
Figure 55:
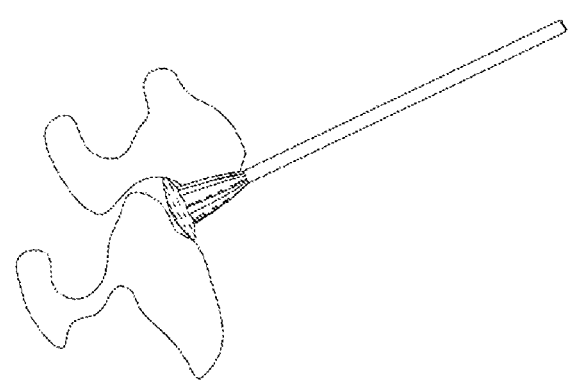

In the FIG. 53 view the lower end of the upper lamina 42 has been milled away and the milling cutter 40 can then be further pushed into the interlaminar gap in order to use the protective arrangement as a lever and to enlarge the interlaminar gap and in order then to be able to continue milling in accordance with the views in FIGS. 54 and 55.

It is to be noted that the Figures shown in the sequence of FIGS. 51 to 55 are shown on an exaggerated scale and do not reproduce the actual dimensions.

In regard to the materials it is to be noted that the milling cutter or the milling head preferably comprises high-quality steel, which can also be the case with the protective arrangements. They can however also comprise plastic, in particular polyetheretherketone (PEEK) or PTFE/Teflon®¬. When the protective arrangement is in the form of a protective ring which is fixed to the threaded pin by way of a nut (embodiment of FIG. 42 or FIG. 46) it has proven to be particularly attractive from the economic point of view for the protective ring to be made of ceramic, being particularly easy to clean and can be used more frequently.

Embodiments provide that the protective arrangement can be deformed by virtue of the geometrical configuration, the selection of an elastic material or a combination of both, in order to be better adapted to the anatomical conditions (for example the narrow gap).

That can be implemented by selecting an elastic material (preferably PTFE/Teflon®, a biocompatible type of silicone or another elastic biocompatible material) and/or the geometrical configuration of the protective arrangement itself, in particular in the region of the above-mentioned intermediate portion. That elastic deformation can involve both the external shape of the protective arrangement and also the position of the protective arrangement with respect to the axis of rotation and the milling surface maximum radius R1 in all three axes. In that respect the elasticity can occur both at the outer peripheral surface of the protective arrangement, or however also due to a partially elastic connection between the protective arrangement and the milling cutter or the seat for connecting the protective arrangement to the milling cutter, for example by the elastic configuration of the coupler, in particular the coupling ball.

Although the proposed milling cutter is particularly suitable for surgery the milling surface which is operative exclusively proximally and the distal protective arrangement can also be used in other areas in milling technology so that protection is also claimed for same.

FIG. 50 once again clearly shows the individual geometries/radii of a milling cutter according to the invention by way of example. Therein the notations are as follows:
R1: milling surface maximum radius
R2: protective arrangement maximum radius
r: radius of the rounded configuration at the radially outer edge at the protective arrangement maximum radius
L: length of the protective arrangement
β: wedge angle of the protective arrangement
β1: wedge angle of the proximal surface of the protective arrangement
β2: wedge angle of the distal surface of the protective arrangement
σ: profile angle of a conical milling surface The subject-matter of the present invention involves not only the subject-matter of the individual claims but also the combination of the individual claims with each other. All features and information disclosed in the documents—including the Abstract—, in particular the spatial configuration illustrated in the drawings, are claimed as being essential to the invention, insofar as they are novel individually or in combination, over the state of the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

LIST OF REFERENCES 2 shaft
4 milling head
4.1 milling surface
4.2 protective ring
4.3 protective cap
6 milling head
6.1 milling surface
6.2 protective ring
6.3 protective cap
8 tissue
10 bone 12 three-dimensional protective zone
14 milling head
14.1 milling surface
14.2 upper circular plate
14.3 lower circular plate
16 protective cap
16.1 insertion opening
16.2 edge
18 milling head
18.1 milling surface
18.3 distal contact surface
20 protective ring
20.1 insertion opening
22 protective cap
22.3 spherical cap
22.4 coupling ball
22.5 seat
22.6 protective ring
24 milling head
24.1 milling surface
24.4 circular plate
24.5 insertion opening
26 milling head
26.1 milling surface
26.3 protective cap
26.4 protective girdle
28 milling head
28.1 milling surface
28.3 protective cap
28.4 protective girdle
30 milling head
30.1 milling surface
30.2 milling surface maximum radius
30.3 insertion opening
32 protective cap
32.4 coupling ball
34 milling head
34.1 milling surface
34.2 protective ring
34.3 distal contact surface
36 milling head
36.1 milling surface
36.2 protective ring
36.3 distal contact surface
38 milling head
38.1 milling surface
38.2 protective ring
38.3 distal contact surface
40 milling cutter
40.1 milling surface
40.2 protective cap
42 upper lamina
44 lower lamina

The invention claimed is:

1. A surgical milling cutter designed for removal of bone or cartilage tissue comprising a shaft which defines a longitudinal axis and which is rotatable about an axis of rotation and which has a nominal diameter and a proximal end which can be non-rotatably connected to a drive unit and a distal end opposite the proximal end, wherein provided at the distal end is a milling head having a milling surface which circumferentially surrounds the shaft and extends along the longitudinal axis of the shaft, wherein the milling surface is delimited by a proximally disposed milling surface proximal end and a distally disposed milling surface distal end and a milling surface maximum radius (R1), wherein the milling cutter is of an atraumatic configuration, the milling surface is also proximally operative, the milling surface is enlarged in a distal direction radially beyond the nominal diameter of the shaft, that a protective arrangement is provided at the distal end, the protective arrangement is provided distally from the milling surface distal end, the protective arrangement has a distal contact surface and a protective arrangement maximum radius (R2) for forming a protective ring which surrounds the milling surface maximum radius (R1) in an annular configuration so that the protective arrangement upon rotation of the milling cutter defines around the milling surface a circumferentially surrounding protective zone extending from the protective arrangement maximum radius (R2) to the milling surface distal end, wherein the protective arrangement maximum radius (R2) is markedly larger than the milling surface maximum radius (R1).

2. The surgical milling cutter according to claim 1, wherein the protective ring narrows radially outwardly.

3. The surgical milling cutter according to claim 2, wherein the protective ring is wedge-shaped.

4. The surgical milling cutter according to claim 3, wherein the protective ring includes a proximal wedge surface which includes a proximal wedge angle ($\beta_1$) with a straight line extending through the milling surface maximum radius (R1).

5. The surgical milling cutter according to claim 3, wherein the protective ring includes a distal wedge surface which includes a distal wedge angle ($\beta_2$) with a straight line extending through the milling surface maximum radius (R1).

6. The surgical milling cutter according to claim 4, wherein the protective ring includes a proximal wedge angle ($\beta_1$) and a distal wedge angle ($\beta_2$).

7. The surgical milling cutter according to claim 6, wherein the proximal wedge angle ($\beta_1$) and the distal wedge angle ($\beta_2$) are of substantially the same size.

8. The surgical milling cutter according to claim 6, wherein the proximal wedge angle ($\beta_1$) and the distal wedge angle ($\beta_2$) are of different sizes.

9. The surgical milling cutter according to claim 6, wherein the distal wedge angle ($\beta_2$) is negative or positive.

10. The surgical milling cutter according to claim 1, wherein the milling surface is of a conical configuration from the milling surface proximal end to the milling surface distal end.

11. The surgical milling cutter according to claim 1, wherein the milling surface includes cutting edges.

12. The milling cutter according to claim 1, wherein the milling surface is adapted to act exclusively proximally.

13. The milling cutter according to claim 1, wherein the protective arrangement maximum radius (R2) corresponds at least to the milling surface maximum radius (R1) plus an upper predetermined limit deviation plus ten times the predetermined concentricity.

14. The milling cutter according to claim 1, wherein the protective arrangement includes a protective cap which forms a distal contact surface and extends to the protective arrangement maximum radius (R2).

15. The milling cutter according to claim 1, wherein the protective arrangement includes a protective girdle which extends in a proximal direction over the protective arrangement maximum radius (R2).

16. The milling cutter according to claim 1, wherein the protective arrangement can be connected to the milling head by way of a connector.

17. The milling cutter according to claim 16, wherein the connector is adapted for releasable connection.

18. The milling cutter according to claim 16, wherein the connector includes a seat provided distally from the milling surface.

19. The milling cutter according to claim 16, wherein the connector includes a stem-mounted coupling ball at a first counterpart joint member, which can be releasably fitted into a corresponding recess having an undercut portion or a constriction at a second counterpart joint member.

20. The milling cutter according to claim 16, wherein the connector is adapted to permit relative displacement between the milling head and the protective arrangement.

21. The A-milling cutter according to claim 16, wherein the connector includes a screw connection.

22. The A-milling cutter according to claim 21, wherein the screw connection includes a threaded pin provided distally from the milling surface and which can be connected to the protective arrangement.

23. The A-milling cutter according to claim 22, wherein the protective arrangement includes a female thread for connection to the threaded pin.

24. The A-milling cutter according to claim 23, wherein the protective arrangement can be connected to the threaded pin by way of a nut and the protective arrangement includes a nut receiver for the nut.

25. The milling cutter according to claim 1, wherein the protective arrangement is of a resistance-reducing nature.

26. The milling cutter according to claim 1, wherein the protective arrangement is at least partially elastic.

27. The milling cutter according to claim 16, wherein at least the connector is elastic.

* * * * *